United States Patent
Dresselhaus et al.

(10) Patent No.: US 7,105,720 B2
(45) Date of Patent: Sep. 12, 2006

(54) EMBRYO SAC-SPECIFIC GENES

(75) Inventors: Thomas Dresselhaus, Hamburg (DE);
Simone Cordts, Ammersbek (DE);
Suseno Amien, Hamburg (DE); Horst Lörz, Hamburg (DE)

(73) Assignee: Advanta Seeds B.V., Kapelle (NL)

( * ) Notice: Subject to any disclaimer, the term of this patent is extended or adjusted under 35 U.S.C. 154(b) by 0 days.

(21) Appl. No.: 10/204,085

(22) PCT Filed: Feb. 28, 2001

(86) PCT No.: PCT/EP01/02258

§ 371 (c)(1),
(2), (4) Date: Oct. 23, 2002

(87) PCT Pub. No.: WO01/64924

PCT Pub. Date: Sep. 7, 2001

(65) Prior Publication Data

US 2003/0115637 A1    Jun. 19, 2003

(30) Foreign Application Priority Data

Mar. 2, 2000    (EP) .................... 00104366

(51) Int. Cl.
*C12N 15/09*    (2006.01)
*C12N 15/29*    (2006.01)
*C12N 15/82*    (2006.01)
*A01H 5/00*    (2006.01)
*A01H 5/10*    (2006.01)

(52) U.S. Cl. .............. 800/278; 800/298; 800/295; 800/320.1; 435/320.1; 435/468; 435/69.1; 536/23.6

(58) Field of Classification Search ............. 536/23.6; 435/69.1, 468, 320.1; 800/278, 279, 320.1, 800/298, 287, 295, 303
See application file for complete search history.

(56) References Cited

FOREIGN PATENT DOCUMENTS

| EP | 0412 006 A1 | * | 6/1991 |
|---|---|---|---|
| WO | WO96/04781 | * | 2/1996 |
| WO | WO97/04116 | * | 2/1997 |
| WO | WO 97/43427 | * | 11/1997 |
| WO | WO98/28430 | * | 7/1998 |
| WO | WO99/18224 | * | 4/1999 |
| WO | WO99/50427 | * | 10/1999 |
| WO | WO99/53083 | * | 10/1999 |
| WO | WO99/57247 | * | 11/1999 |

OTHER PUBLICATIONS

Drews et al . The Plant Cell, vol. 10, pp. 5-17 (1998).*
Sauter et al. Sex Plant Reprod (1998) 11:41-48.*
Vollbrecht et al. Developmental Genetics (1995) 16:44-63.*
Cords et al. The Plant Journal (2001) 25(1):103-114.*
DATABASE EMBL, Accession No. AI668414 (Deposited, May 17, 1999).*
Cordts et al. Plant Journal (2001) 25(1):103-114.*
DATABASE EMBL Accession No. AF082130, Feb. 8, 1999.*
DATABASE EMBL Accession No. AI649573, May 4, 1999.*
DATABASE EMBL Accession No. U68407, Nov. 5, 1996.*

* cited by examiner

*Primary Examiner*—Medina A. Ibrahim
(74) *Attorney, Agent, or Firm*—Norris McLaughlin & Marcus P.A; Christa Hildebrand

(57) ABSTRACT

The present invention relates to isolated nucleotide sequences useful for the production of plants with a modified embryo sac, embryo and/or endosperm development, and to transgenic cells and plants transformed with the nucleotide sequences.

28 Claims, 3 Drawing Sheets

SEQUENCE LISTING

<160> NUMBER OF SEQ ID NOS: 45

<210> SEQ ID NO 1
<211> LENGTH: 606
<212> TYPE: DNA
<213> ORGANISM: Zea mays

<400> SEQUENCE: 1

```
gaatagttcc accacgttac ttccatatat atttcccttg gattggattg gatcgtcggc    60
gcccaaacga ataataatcc ggcaatggag ccttcacgag ggaagctgtc tgccgccgcc   120
gtcctcctgc tgatgacgac gctcctcgtg gtggccgcca tgcgggcggt tgaggcacgc   180
gactgcctga cacagagcac ccggttaccg gggcacctgt gcgtgcggtc ggactactgc   240
gcgatcgggt gcaggcgga gggcaagggc tacacgggcg caggtgcct catctctccc     300
atcccgctcg acgggattct ctgctactgc gtcaagccgt gcccatccaa cacgacgaca   360
taatgatgag acaaagggcg gtgggtgcag tgcacgctgg ccggggtta tcagtccaca    420
catcctaccg tacgtgtctg tgttaataac ttttttttgt cttggaagtc tgtggtggta   480
atgactttta aatgtcttgg aataaaccgg gttctagtcc cttataagct agcagtactg   540
taacaattca gatcatcaaa gacagcagga accggtggt tgagttgaaa aaaaaaaaa    600
aaaaaa                                                              606
```

<210> SEQ ID NO 2
<211> LENGTH: 537
<212> TYPE: DNA
<213> ORGANISM: Zea mays

<400> SEQUENCE: 2

```
gatagttcca ccacgttact tccatatatt tcccttggat tggatcgtcg gcgcccaaac    60
gaacaataat ccggcaatgg agtcttcacg agggaagctg tctgccgccg cgtcctcct   120
gctaatgacg ctcctcatgg tggccgccat gcgggcggtt gaggcacgag actgcctgac   180
gcagagtacc cggttaccgg ggcatctgtg cgtgcggtcg gactactgcg cgatcgggtg   240
cagggcggag ggcaagggct acacgggcg caggtgcctc atctctccca tcccgctcga   300
cgggattctc tgctactgcg tcaagccttg cacatccacc acgacagaat gatgagacaa   360
gagcggtggg tgcagtgcag gctgatcggg gggttatcag ttatatatgg acatcctacc   420
gtgtctgtta ataacttgta aatgtcttgg gaagtttgtg gtgataagtt ttaaatgtct   480
tggaataaag tgggttctat atagacttct actcgttaaa aaaaaaaaa aaaaaaa     537
```

<210> SEQ ID NO 3
<211> LENGTH: 519
<212> TYPE: DNA
<213> ORGANISM: Zea mays

<400> SEQUENCE: 3

```
ggatagttcc accacgttac ttccatatat ttcccttgga ttggatcgtc ggcgcccaaa    60
cgaatactaa tccggcaatg gagtcttcac gagggaagct gtctgccgcc gccgtcctcc   120
tgctaatgac gctcccttatg gtggccgcca tgcgggcggt tgaggcacgc gactgcctga   180
cacagagcac ccggttaccg gggcatctgt gcgtgcggtc ggactactgc gcgatcgggt   240
gcagggcgga gggcaagggc tacacgggcg caggtgcct catctctccc atcccgctcg    300
acgggattct ctgctactgc gtcaagcctt gcacatccac cacgacagaa tgatgagaca   360
```

```
agagcggtgg gtgcagtgca ggctgatcgg ggggttatca gttatatatg acatcctac      420 cgtgtctgtt aataacttgt aaatgtcttg ggaagtttgt ggtgataagt tttaaatgtc     480
ttggaataaa gtgggttcta taaaaaaaaa aaaaaaaaa                            519

<210> SEQ ID NO 4
<211> LENGTH: 601
<212> TYPE: DNA
<213> ORGANISM: Zea mays

<400> SEQUENCE: 4
gatatagttc caccacatta cttccatata tttcccttgg attggatcgt cggcgccaaa      60
acgaataata atccggcaat ggagtcttca cgagggaagc tgtctgccgc cggcgtcctc     120
ctgctaatga cgctcctcat ggtggccgcc atgcgggcgg ttgaggcacg agactgcctg     180
acgcagagta cccggttacc ggggcatctg tgcgtgcggt cggactactg cgcgatcggg     240
tgcagggcgg agggcaaggg ctacacgggc ggcaggtgcc ttatctctcc catcacgctc     300
gacgggattc tctgctactg cgtcaagcct tgcacatcca ccacgacaaa atgatgagac     360
aagacaagag cggtgggtgc aatgcaggct gaccgggggt tatcagttat atatggacat     420
cctaccgtgt ctgttaataa cttgtaaatg tcttgggaaa gtttgtggtg ataagtttta     480
aatgtcttgg aataaagtgg gttctataca gacttctact cgttaagttg ttggattact     540
actactgctg ttttttattt gaggaattac tgctttgttt ttaaaaaaaa aaaaaaaaa     600 a                                                                     601

<210> SEQ ID NO 5
<211> LENGTH: 276
<212> TYPE: DNA
<213> ORGANISM: Zea mays

<400> SEQUENCE: 5
atggagcctt cacgagggaa gctgtctgcc gccgccgtcc tcctgctgat gacgacgctc      60
ctcgtggtgg ccgccatgcg ggcggttgag gcacgcgact gcctgacaca gagcacccgg     120
ttaccggggc acctgtgcgt gcggtcggac tactgcgcga tcgggtgcag ggcggagggc     180
aagggctaca cggcggcag gtgcctcatc tctcccatcc cgctcgacgg gattctctgc     240
tactgcgtca agccgtgccc atccaacacg acgaca                               276

<210> SEQ ID NO 6
<211> LENGTH: 273
<212> TYPE: DNA
<213> ORGANISM: Zea mays

<400> SEQUENCE: 6
atggagtctt cacgagggaa gctgtctgcc gccggcgtcc tcctgctaat gacgctcctc      60
atggtggccg ccatgcgggc ggttgaggca cgagactgcc tgacgcagag tacccggtta     120
ccggggcatc tgtgcgtgcg gtcggactac tgcgcgatcg gtgcagggc ggagggcaag     180 ggctacacgg gcggcaggtg cctcatctct cccatcccgc tcgacgggat tctctgctac     240
tgcgtcaagc cttgcacatc caccacgaca gaa                                  273

<210> SEQ ID NO 7
<211> LENGTH: 273
<212> TYPE: DNA
<213> ORGANISM: Zea mays
```

<400> SEQUENCE: 7

```
atggagtctt cacgagggaa gctgtctgcc gccgccgtcc tcctgctaat gacgctcctt    60
atggtggccg ccatgcgggc ggttgaggca cgcgactgcc tgacacagag cacccggtta   120
ccggggcatc tgtgcgtgcg gtcggactac tgcgcgatcg ggtgcagggc ggagggcaag   180
ggctacacgg gcggcaggtg cctcatctct cccatcccgc tcgacgggat tctctgctac   240
tgcgtcaagc cttgcacatc caccacgaca gaa                                273
```

<210> SEQ ID NO 8
<211> LENGTH: 273
<212> TYPE: DNA
<213> ORGANISM: Zea mays

<400> SEQUENCE: 8

```
atggagtctt cacgagggaa gctgtctgcc gccggcgtcc tcctgctaat gacgctcctc    60
atggtggccg ccatgcgggc ggttgaggca cgagactgcc tgacgcagag tacccggtta   120
ccggggcatc tgtgcgtgcg gtcggactac tgcgcgatcg ggtgcagggc ggagggcaag   180
ggctacacgg gcggcaggtg ccttatctct cccatcacgc tcgacgggat tctctgctac   240
tgcgtcaagc cttgcacatc caccacgaca aaa                                273
```

<210> SEQ ID NO 9
<211> LENGTH: 92
<212> TYPE: PRT
<213> ORGANISM: Zea mays

<400> SEQUENCE: 9

```
Met Glu Pro Ser Arg Gly Lys Leu Ser Ala Ala Val Leu Leu Leu
 1               5                  10                  15

Met Thr Thr Leu Leu Val Val Ala Ala Met Arg Ala Val Glu Ala Arg
                 20                  25                  30

Asp Cys Leu Thr Gln Ser Thr Arg Leu Pro Gly His Leu Cys Val Arg
             35                  40                  45

Ser Asp Tyr Cys Ala Ile Gly Cys Arg Ala Glu Gly Lys Gly Tyr Thr
     50                  55                  60

Gly Gly Arg Cys Leu Ile Ser Pro Ile Pro Leu Asp Gly Ile Leu Cys
 65                  70                  75                  80

Tyr Cys Val Lys Pro Cys Pro Ser Asn Thr Thr Thr
                 85                  90
```

<210> SEQ ID NO 10
<211> LENGTH: 91
<212> TYPE: PRT
<213> ORGANISM: Zea mays

<400> SEQUENCE: 10

```
Met Glu Ser Ser Arg Gly Lys Leu Ser Ala Ala Gly Val Leu Leu Leu
 1               5                  10                  15

Met Thr Leu Leu Met Val Ala Ala Met Arg Ala Val Glu Ala Arg Asp
                 20                  25                  30

Cys Leu Thr Gln Ser Thr Arg Leu Pro Gly His Leu Cys Val Arg Ser
             35                  40                  45

Asp Tyr Cys Ala Ile Gly Cys Arg Ala Glu Gly Lys Gly Tyr Thr Gly
     50                  55                  60

Gly Arg Cys Leu Ile Ser Pro Ile Pro Leu Asp Gly Ile Leu Cys Tyr
 65                  70                  75                  80
```

Cys Val Lys Pro Cys Thr Ser Thr Thr Thr Glu
            85                  90

<210> SEQ ID NO 11
<211> LENGTH: 91
<212> TYPE: PRT
<213> ORGANISM: Zea mays

<400> SEQUENCE: 11

Met Glu Ser Ser Arg Gly Lys Leu Ser Ala Ala Val Leu Leu Leu
 1               5                  10                  15

Met Thr Leu Leu Met Val Ala Ala Met Arg Ala Val Glu Ala Arg Asp
            20                  25                  30

Cys Leu Thr Gln Ser Thr Arg Leu Pro Gly His Leu Cys Val Arg Ser
            35                  40                  45

Asp Tyr Cys Ala Ile Gly Cys Arg Ala Glu Gly Lys Gly Tyr Thr Gly
        50                  55                  60

Gly Arg Cys Leu Ile Ser Pro Ile Pro Leu Asp Gly Ile Leu Cys Tyr
 65                  70                  75                  80

Cys Val Lys Pro Cys Thr Ser Thr Thr Thr Glu
            85                  90

<210> SEQ ID NO 12
<211> LENGTH: 91
<212> TYPE: PRT
<213> ORGANISM: Zea mays

<400> SEQUENCE: 12

Met Glu Ser Ser Arg Gly Lys Leu Ser Ala Ala Gly Val Leu Leu Leu
 1               5                  10                  15

Met Thr Leu Leu Met Val Ala Ala Met Arg Ala Val Glu Ala Arg Asp
            20                  25                  30

Cys Leu Thr Gln Ser Thr Arg Leu Pro Gly His Leu Cys Val Arg Ser
            35                  40                  45

Asp Tyr Cys Ala Ile Gly Cys Arg Ala Glu Gly Lys Gly Tyr Thr Gly
        50                  55                  60

Gly Arg Cys Leu Ile Ser Pro Ile Thr Leu Asp Gly Ile Leu Cys Tyr
 65                  70                  75                  80

Cys Val Lys Pro Cys Thr Ser Thr Thr Thr Lys
            85                  90

<210> SEQ ID NO 13
<211> LENGTH: 1204
<212> TYPE: DNA
<213> ORGANISM: Zea mays

<400> SEQUENCE: 13
tggaagaatt cggatctact ggcggaaaca gaaagttttt gttcctcgaa cttcgatata      60
aaaagacata ggagaagcct cttatgtttt aaaatagaat ttcacagaga tagacataat     120
gaagtattag aactctcaca gaagtcatac atagaaaagc actaaagaag tacagtatgc     180
atcagtgtaa ggccgcgcct gcgccaaaag tcaagggtga taagtttggg aatcatcagt     240
gtccccagat tcagtgtcag aaagatcaga taaagtcagt accatatgct tctactatca     300
gaagcatttt gtatgctcaa atatatattc accctgactt agaatttact accgggatgc     360
ttgggagata tcgtgtatat ctggcaccta tgtttatgac agtgaagctc accatctttta    420
ttctattgac attcattttc atgcaaatta cataacgtat ggtagaacga ccgaatgcaa     480

| | |
|---|---|
| attactgcta ataaacatcc tgcgtgcgcg caatggtgca ccatctacca attaatagct | 540 |
| gtaacggtac tgcaagtaat ggtcgaagcg ttataccgta caggattata tatatacaca | 600 |
| tgcctctcga acggcttcaa tagttccacc acgttacttc catatatatt tcccttggat | 660 |
| tggattggat cgtcggcgcc caaacgaata ataatccggc aatggagcct tcacgaggga | 720 |
| agctgtctgc cgccgccgtc ctcctgctga tgacgacgct cctcgtggtg gccgccatgc | 780 |
| gggcggttga ggcacgcgac tgcctgacac agagcacccg gttaccgggg cacctgtgcg | 840 |
| tgcggtcgga ctactgcgcg atcgggtgca gggcggaggg caagggctac acgggcggca | 900 |
| ggtgcctcat ctctcccatc ccgctcgacg ggattctctg ctactgcgtc aagccgtgcc | 960 |
| catccaacac gacgacataa tgatgagaca aagggcggtg ggtgcagtgc acgctggccg | 1020 |
| ggggttatca gtccacacat cctaccgtac gtgtctgtgt taataacttt tttttgtctt | 1080 |
| ggaagtctgt ggtggtaatg acttttaaat gtcttggaat aaaccgggtt ctagtcccctt | 1140 |
| ataagctagc agtactgtaa caattcagat catcaaagac agcaggaaac cggtggttga | 1200 |
| gttg | 1204 |

<210> SEQ ID NO 14
<211> LENGTH: 2430
<212> TYPE: DNA
<213> ORGANISM: Zea mays

<400> SEQUENCE: 14

| | |
|---|---|
| cgacggcccg ggctggtatc tgtgtgtatc tggcacctat gtttatgaca gagaaactca | 60 |
| ccatgtttat tctattgaca ttcattttca tgcaaattac ataacgtatg ctagaaccaa | 120 |
| atgcaaatta ctgctaataa acatgttgca taacgtactc tctgccgctg cggtcgccgt | 180 |
| gcctctcgcg tccattgatg cgatgtgaat catcgatgca gagactagac atccctttc | 240 |
| tcgcgccgca acatgttatt ggttattgat ctactggtca tgtactcatg tcatttagat | 300 |
| gtaaggtcag atttgttcat ttgtacgtat tatttaggtg ccgtgaatgt gaagcgaatg | 360 |
| tctctgtatg cgtgtgagtt gggtgccgta gttctgatga cgcatgtgg atatatacta | 420 |
| tgtatatatg acacgacaca aaacttcagt acagcgatgg attgtattta taccggtttg | 480 |
| gaatcagaat gcagcatcct gtttttttt ggattgattg atcctgcatg catggccgtg | 540 |
| tgttggggga atctgagcgt caatcactgt gatgagtatc agtggtggtg ctttctgtga | 600 |
| aggcacggac ggtccgcaac gggaaactgg acggtccgtg acctggcgca gaggatacgg | 660 |
| tttccgtctg accagacgaa cggacggtcc gcacgtgcgc agggacaacg gagttcgccg | 720 |
| aacagtacct ggatcttgct ctccggagag acccgtcgag gaagagaaat cctaggattt | 780 |
| gtcttgaaat cagtaggcca cctaagacgc ctctaaacga gagaggtgaa gattagagag | 840 |
| agaaaactat gttactgtct actcctaggg gaaaaggtaa ataacagaag ataatttgat | 900 |
| tattgattcg attgttggtt cttcaatcgg tcgtacccct caaatatata agggggtct | 960 |
| agatccattc caaaacgttc tccaacagct cccacgggat taagggcta aacacacgag | 1020 |
| gagatagaaa ttttaaccgc ttgatttgat ctattcgtgg accgtctgca cctatgggcg | 1080 |
| gaccatccac gggccggacc atttagccgt gctcagtgtc acaaatggag ctcaacacat | 1140 |
| gccctcctgc ctttaggaga agctgagcga accaaaagca ctgacacagg ccggaaccga | 1200 |
| ctcgaaatgt tcacatcggt tctcttaagc atctgccaca tactagatga cgttaacaga | 1260 |
| aaatcacgtc aacgtctgca cagtcatggc tcgcccgagg tctccccagg atggcctcgc | 1320 |
| gcgagcgtga ctgtgtctcc cgtccgaggg tggcctcaag cgacaaacat agaaccatga | 1380 |

-continued

```
tgtactatag atctatatct atgtttacag tacatcaaca gattatgaag tctatttcag      1440
gttgaatgag gtttatcctc ggacgagtga tatttgtcgt ttcatattta tgttttatat      1500 aaattttac tctcgacaca atgcattgtc acataccgat tcaaattcaa atatatgtgc      1560
gattctgtgc tcatattgtg cgattctgcg ctcatatggc acctatgttt atgacagtga      1620
aactcacaat gttattcta ttgacattca ttttcatgca aattacataa cgtatgctag      1680
aaccaaatgc aaattactgc taataaacat cctgcgtaag cgcaatggcg caccatttac      1740
caatagctgt aacggtgcaa gtacgtaata gttggagcgt tatgtttctc tcctctcttc      1800
ccaccgtaca ggatcatata tatacacatg cctctagaac ggcttcaata tatagttcca      1860
ccacattact tccatatatt tcccttggat tggatcgtcg cgccaaaac gaataataat       1920 ccggcaatgg agtcttcacg agggaagctg tctgccgccg gcgtcctcct gctaatgacg      1980
ctcctcatgg tggccgccat gcgggcggtt gaggcacgag actgcctgac gcagagtacc      2040
cggttaccgg ggcatctgtg cgtgcggtcg gactactgcg cgatcgggtg cagggcggag      2100
ggcaagggct acacggggcgg caggtgcctt atctctccca tcacgctcga cgggattctc     2160
tgctactgcg tcaagccttg cacatccacc acgacaaaat gatgagacaa gacaagagcg      2220
gtgggtgcaa tgcaggctga ccggggggtta tcagttatat atggacatcc taccgtgtct    2280
gttaataact tgtaaatgtc ttgggaaagt ttgtggtgat aagttttaaa tgtcttggaa      2340
taaagtgggt tctatacaga cttctactcg ttaagttgtt ggattactac tactgctgtt     2400 tttatttga ggaattactg ctttgttttt                                        2430
```

<210> SEQ ID NO 15
<211> LENGTH: 701
<212> TYPE: DNA
<213> ORGANISM: Zea mays

<400> SEQUENCE: 15

```
tggaagaatt cggatctact ggcggaaaca gaaagttttt gttcctcgaa cttcgatata       60
aaaagacata ggagaagcct cttatgtttt aaaatagaat ttcacagaga tagacataat      120
gaagtattag aactctcaca gaagtcatac atagaaaagc actaagaag tacagtatgc       180 atcagtgtaa ggccgcgcct gcgccaaaag tcaagggtga taagtttggg aatcatcagt     240
gtccccagat tcagtgtcag aaagatcaga taaagtcagt accatatgct tctactatca     300
gaagcatttt gtatgctcaa atatatattc accctgactt agaatttact accgggatgc     360
ttgggagata tcgtgtatat ctggcaccta tgtttatgac agtgaagctc accatcttta     420
ttctattgac attcattttc atgcaaatta cataacgtat ggtagaacga ccgaatgcaa     480
attactgcta ataaacatcc tgcgtgcgcg caatggtgca ccatctacca attaatagct    540
gtaacggtac tgcaagtaat ggtcgaagcg ttataccgta caggattata tatacaca      600 tgcctctcga acggcttcaa tagttccacc acgttacttc catatatatt tcccttggat    660
tggattggat cgtcggcgcc caaacgaata ataatccggc a                         701
```

<210> SEQ ID NO 16
<211> LENGTH: 201
<212> TYPE: DNA
<213> ORGANISM: Zea mays

<400> SEQUENCE: 16

```
tgcgtgcgcg caatggtgca ccatctacca attaatagct gtaacggtac tgcaagtaat       60
```

```
ggtcgaagcg ttataccgta caggattata tatatacaca tgcctctcga acggcttcaa      120
tagttccacc acgttacttc catatatatt tcccttggat tggattggat cgtcggcgcc      180
caaacgaata ataatccggc a                                                201

<210> SEQ ID NO 17
<211> LENGTH: 501
<212> TYPE: DNA
<213> ORGANISM: Zea mays

<400> SEQUENCE: 17
gcgccaaaag tcaagggtga taagtttggg aatcatcagt gtccccagat tcagtgtcag       60
aaagatcaga taaagtcagt accatatgct tctactatca gaagcatttt gtatgctcaa      120
atatatattc accctgactt agaatttact accgggatgc ttgggagata tcgtgtatat      180
ctggcaccta tgtttatgac agtgaagctc accatcttta ttctattgac attcattttc      240
atgcaaatta cataacgtat ggtagaacga ccgaatgcaa attactgcta ataaacatcc      300
tgcgtgcgcg caatggtgca ccatctacca attaatagct gtaacggtac tgcaagtaat      360
ggtcgaagcg ttataccgta caggattata tatatacaca tgcctctcga acggcttcaa      420
tagttccacc acgttacttc catatatatt tcccttggat tggattggat cgtcggcgcc      480
caaacgaata ataatccggc a                                                501

<210> SEQ ID NO 18
<211> LENGTH: 83
<212> TYPE: DNA
<213> ORGANISM: Zea mays

<400> SEQUENCE: 18
aatagttcca ccacgttact tccatatata tttcccttgg attggattgg atcgtcggcg       60
cccaaacgaa taataatccg gca                                               83

<210> SEQ ID NO 19
<211> LENGTH: 76
<212> TYPE: DNA
<213> ORGANISM: Zea mays

<400> SEQUENCE: 19
gatagttcca ccacgttact tccatatatt tcccttggat tggatcgtcg gcgcccaaac       60
gaacaataat ccggca                                                       76

<210> SEQ ID NO 20
<211> LENGTH: 77
<212> TYPE: DNA
<213> ORGANISM: Zea mays

<400> SEQUENCE: 20
ggatagttcc accacgttac ttccatatat ttcccttgga ttggatcgtc ggcgcccaaa       60
cgaatactaa tccggca                                                      77

<210> SEQ ID NO 21
<211> LENGTH: 78
<212> TYPE: DNA
<213> ORGANISM: Zea mays

<400> SEQUENCE: 21
gatatagttc caccacatta cttccatata tttcccttgg attggatcgt cggcgccaaa       60
acgaataata atccggca                                                     78
```

<210> SEQ ID NO 22
<211> LENGTH: 246
<212> TYPE: DNA
<213> ORGANISM: Zea mays

<400> SEQUENCE: 22

| | |
|---|---|
| taatgatgag acaaagggcg gtgggtgcag tgcacgctgg ccgggggtta tcagtccaca | 60 |
| catcctaccg tacgtgtctg tgttaataac ttttttttgt cttggaagtc tgtggtggta | 120 |
| atgacttta aatgtcttgg aataaaccgg gttctagtcc cttataagct agcagtactg | 180 |
| taacaattca gatcatcaaa gacagcagga aaccggtggt tgagttgaaa aaaaaaaaa | 240 |
| aaaaaa | 246 |

<210> SEQ ID NO 23
<211> LENGTH: 188
<212> TYPE: DNA
<213> ORGANISM: Zea mays

<400> SEQUENCE: 23

| | |
|---|---|
| tgatgagaca agagcggtgg gtgcagtgca ggctgatcgg ggggttatca gttatatatg | 60 |
| gacatcctac cgtgtctgtt aataacttgt aaatgtcttg gaagtttgt ggtgataagt | 120 |
| tttaaatgtc ttggaataaa gtgggttcta tatagacttc tactcgttaa aaaaaaaaaa | 180 |
| aaaaaaaa | 188 |

<210> SEQ ID NO 24
<211> LENGTH: 169
<212> TYPE: DNA
<213> ORGANISM: Zea mays

<400> SEQUENCE: 24

| | |
|---|---|
| tgatgagaca agagcggtgg gtgcagtgca ggctgatcgg ggggttatca gttatatatg | 60 |
| gacatcctac cgtgtctgtt aataacttgt aaatgtcttg gaagtttgt ggtgataagt | 120 |
| tttaaatgtc ttggaataaa gtgggttcta taaaaaaaaa aaaaaaaa | 169 |

<210> SEQ ID NO 25
<211> LENGTH: 250
<212> TYPE: DNA
<213> ORGANISM: Zea mays

<400> SEQUENCE: 25

| | |
|---|---|
| tgatgagaca agacaagagc ggtgggtgca atgcaggctg accgggggtt atcagttata | 60 |
| tatggacatc ctaccgtgtc tgttaataac ttgtaaatgt cttgggaaag tttgtggtga | 120 |
| taagttttaa atgtcttgga ataaagtggg ttctatacag acttctactc gttaagttgt | 180 |
| tggattacta ctactgctgt tttttatttg aggaattact gctttgtttt taaaaaaaaa | 240 |
| aaaaaaaaaa | 250 |

<210> SEQ ID NO 26
<211> LENGTH: 1926
<212> TYPE: DNA
<213> ORGANISM: Zea mays

<400> SEQUENCE: 26

| | |
|---|---|
| cgacggcccg ggctggtatc tgtgtgtatc tggcacctat gtttatgaca gagaaactca | 60 |
| ccatgtttat tctattgaca ttcattttca tgcaaattac ataacgtatg ctagaaccaa | 120 |

-continued

```
atgcaaatta ctgctaataa acatgttgca taacgtactc tctgccgctg cggtcgccgt      180
gcctctcgcg tccattgatg cgatgtgaat catcgatgca gagactagac atcccttttc      240
tcgcgccgca acatgttatt ggttattgat ctactggtca tgtactcatg tcatttagat      300
gtaaggtcag atttgttcat ttgtacgtat tatttaggtg ccgtgaatgt gaagcgaatg      360
tctctgtatg cgtgtgagtt gggtgccgta gttctgatga cgcatgtgg atatatacta       420 tgtatatatg acacgacaca aaacttcagt acagcgatgg attgtattta taccggtttg      480
gaatcagaat gcagcatcct gtttttttt ggattgattg atcctgcatg catggccgtg       540
tgttggggga atctgagcgt caatcactgt gatgagtatc agtggtggtg ctttctgtga      600
aggcacggac ggtccgcaac gggaaactgg acggtccgtg acctggcgca gaggatacgg      660
tttccgtctg accagacgaa cggacggtcc gcacgtgcgc agggacaacg gagttcgccg      720
aacagtacct ggatcttgct ctccggagag acccgtcgag gaagagaaat cctaggattt      780
gtcttgaaat cagtaggcca cctaagacgc ctctaaacga gagaggtgaa gattagagag      840
agaaaactat gttactgtct actcctaggg gaaaaggtaa ataacagaag ataatttgat     900
tattgattcg attgttggtt cttcaatcgg tcgtacccct caaatatata aggggggtct     960
agatccattc caaaacgttc tccaacagct cccacgggat taaagggcta acacacgag     1020 gagatagaaa ttttaaccgc ttgatttgat ctattcgtgg accgtctgca cctatgggcg     1080
gaccatccac gggccggacc atttagccgt gctcagtgtc acaaatggag ctcaacacat     1140
gccctcctgc ctttaggaga agctgagcga accaaaagca ctgacacagg ccggaaccga     1200
ctcgaaatgt tcacatcggt tctcttaagc atctgccaca tactagatga cgttaacaga     1260
aaatcacgtc aacgtctgca cagtcatggc tcgcccgagg tctccccagg atggcctcgc     1320
gcgagcgtga ctgtgtctcc cgtccgaggg tggcctcaag cgacaaacat agaaccatga     1380
tgtactatag atctatatct atgtttacag tacatcaaca gattatgaag tctatttcag     1440
gttgaatgag gtttatcctc ggacgagtga tatttgtcgt ttcatattta tgttttatat     1500 aaattttttac tctcgacaca atgcattgtc ataccgat tcaaattcaa atatatgtgc      1560
gattctgtgc tcatattgtg cgattctgcg ctcatatggc acctatgttt atgacagtga     1620
aactcacaat gtttattcta ttgacattca ttttcatgca aattacataa cgtatgctag     1680
aaccaaatgc aaattactgc taataaacat cctgcgtaag cgcaatggcg caccatttac     1740
caatagctgt aacggtgcaa gtacgtaata gttggagcgt tatgtttctc tcctctcttc     1800
ccaccgtaca ggatcatata tatacacatg cctctagaac ggcttcaata tatagttcca     1860
ccacattact tccatatatt tcccttggat tggatcgtcg gcgccaaaac gaataataat     1920
ccggca                                                               1926
```

<210> SEQ ID NO 27
<211> LENGTH: 227
<212> TYPE: DNA
<213> ORGANISM: Zea mays

<400> SEQUENCE: 27

```
ctaataaaca tcctgcgtaa gcgcaatggc gcaccattta ccaatagctg taacggtgca      60
agtacgtaat agttggagcg ttatgtttct ctcctctctt cccaccgtac aggatcatat     120
atatacacat gcctctagaa cggcttcaat atatagttcc accacattac ttccatatat     180
ttcccttgga ttggatcgtc ggcgccaaaa cgaataataa tccggca                   227
```

<210> SEQ ID NO 28
<211> LENGTH: 427
<212> TYPE: DNA
<213> ORGANISM: Zea mays

<400> SEQUENCE: 28

| | | |
|---|---|---|
| taaattttta ctctcgacac aatgcattgt cacataccga ttcaaattca aatatatgtg | 60 |
| cgattctgtg ctcatattgt gcgattctgc gctcatatgg cacctatgtt tatgacagtg | 120 |
| aaactcacaa tgtttattct attgacattc attttcatgc aaattacata acgtatgcta | 180 |
| gaaccaaatg caaattactg ctaataaaca tcctgcgtaa gcgcaatggc gcaccattta | 240 |
| ccaatagctg taacggtgca agtacgtaat agttggagcg ttatgtttct ctcctctctt | 300 |
| cccaccgtac aggatcatat atatacacat gcctctagaa cggcttcaat atatagttcc | 360 |
| accacattac ttccatatat ttcccttgga ttggatcgtc ggcgccaaaa cgaataataa | 420 |
| tccggca | 427 |

<210> SEQ ID NO 29
<211> LENGTH: 927
<212> TYPE: DNA
<213> ORGANISM: Zea mays

<400> SEQUENCE: 29

| | | |
|---|---|---|
| ttaaagggct aaacacacga ggagatagaa attttaaccg cttgatttga tctattcgtg | 60 |
| gaccgtctgc acctatgggc ggaccatcca cgggccggac catttagccg tgctcagtgt | 120 |
| cacaaatgga gctcaacaca tgccctcctg cctttaggaa aagctgagcg aaccaaaagc | 180 |
| actgacacag gccggaaccg actcgaaatg ttcacatcgg ttctcttaag catctgccac | 240 |
| atactagatg acgttaacag aaaatcacgt caacgtctgc acagtcatgg ctcgcccgag | 300 |
| gtctccccag gatggcctcg cgcgagcgtg actgtgtctc ccgtccgagg gtggcctcaa | 360 |
| gcgacaaaca tagaaccatg atgtactata gatctatatc tatgtttaca gtacatcaac | 420 |
| agattatgaa gtctatttca ggttgaatga ggtttatcct cggacgagtg atatttgtcg | 480 |
| tttcatatttt atgttttata taaattttta ctctcgacac aatgcattgt cacataccga | 540 |
| ttcaaattca aatatatgtg cgattctgtg ctcatattgt gcgattctgc gctcatatgg | 600 |
| cacctatgtt tatgacagtg aaactcacaa tgtttattct attgacattc attttcatgc | 660 |
| aaattacata acgtatgcta gaaccaaatg caaattactg ctaataaaca tcctgcgtaa | 720 |
| gcgcaatggc gcaccattta ccaatagctg taacggtgca agtacgtaat agttggagcg | 780 |
| ttatgtttct ctcctctctt cccaccgtac aggatcatat atatacacat gcctctagaa | 840 |
| cggcttcaat atatagttcc accacattac ttccatatat ttcccttgga ttggatcgtc | 900 |
| ggcgccaaaa cgaataataa tccggca | 927 |

<210> SEQ ID NO 30
<211> LENGTH: 1427
<212> TYPE: DNA
<213> ORGANISM: Zea mays

<400> SEQUENCE: 30

| | | |
|---|---|---|
| tgttttttt tggattgatt gatcctgcat gcatggccgt gtgttggggg aatctgagcg | 60 |
| tcaatcactg tgatgagtat cagtggtggt gctttctgtg aaggcacgga cggtccgcaa | 120 |
| cgggaaactg gacggtccgt gacctggcgc agaggatacg gtttccgtct gaccagacga | 180 |
| acggacggtc cgcacgtgcg cagggacaac ggagttcgcc gaacagtacc tggatcttgc | 240 |

-continued

| | |
|---|---|
| tctccggaga gacccgtcga ggaagagaaa tcctaggatt tgtcttgaaa tcagtaggcc | 300 |
| acctaagacg cctctaaacg agagaggtga agattagaga gagaaaacta tgttactgtc | 360 |
| tactcctagg ggaaaaggta aataacagaa gataatttga ttattgattc gattgttggt | 420 |
| tcttcaatcg gtcgtacccc tcaaatatat aaggggggtc tagatccatt ccaaaacgtt | 480 |
| ctccaacagc tcccacggga ttaaagggct aaacacacga ggagatagaa attttaaccg | 540 |
| cttgatttga tctattcgtg gaccgtctgc acctatgggc ggaccatcca cgggccggac | 600 |
| catttagccg tgctcagtgt cacaaatgga gctcaacaca tgccctcctg cctttaggag | 660 |
| aagctgagcg aaccaaaagc actgacacag gccggaaccg actcgaaatg ttcacatcgg | 720 |
| ttctcttaag catctgccac atactagatg acgttaacag aaaatcacgt caacgtctgc | 780 |
| acagtcatgg ctcgcccgag gtctccccag gatggcctcg cgcgagcgtg actgtgtctc | 840 |
| ccgtccgagg gtggcctcaa gcgacaaaca tagaaccatg atgtactata gatctatatc | 900 |
| tatgtttaca gtacatcaac agattatgaa gtctatttca ggttgaatga ggtttatcct | 960 |
| cggacgagtg atatttgtcg tttcatattt atgttttata taaatttttta ctctcgacac | 1020 |
| aatgcattgt cacataccga ttcaaattca aatatatgtg cgattctgtg ctcatattgt | 1080 |
| gcgattctgc gctcatatgg cacctatgtt tatgacagtg aaactcacaa tgtttattct | 1140 |
| attgacattc attttcatgc aaattacata acgtatgcta gaaccaaatg caaattactg | 1200 |
| ctaataaaca tcctgcgtaa gcgcaatggc gcaccattta ccaatagctg taacggtgca | 1260 |
| agtacgtaat agttggagcg ttatgtttct ctcctctctt cccaccgtac aggatcatat | 1320 |
| atatacacat gcctctagaa cggcttcaat atatagttcc accacattac ttccatatat | 1380 |
| ttcccttgga ttggatcgtc ggcgccaaaa cgaataataa tccggca | 1427 |

<210> SEQ ID NO 31
<211> LENGTH: 1727
<212> TYPE: DNA
<213> ORGANISM: Zea mays

<400> SEQUENCE: 31

| | |
|---|---|
| gcgatgtgaa tcatcgatgc agagactaga catcccttt ctcgcgccgc aacatgttat | 60 |
| tggttattga tctactggtc atgtactcat gtcatttaga tgtaaggtca gatttgttca | 120 |
| tttgtacgta ttatttaggt gccgtgaatg tgaagcgaat gtctctgtat gcgtgtgagt | 180 |
| tgggtgccgt agttctgatg agcgcatgtg gatatatact atgtatatat gacacgacac | 240 |
| aaaacttcag tacagcgatg gattgtattt ataccggttt ggaatcagaa tgcagcatcc | 300 |
| tgttttttt tggattgatt gatcctgcat gcatggccgt gtgttggggg aatctgagcg | 360 |
| tcaatcactg tgatgagtat cagtggtggt gctttctgtg aaggcacgga cggtccgcaa | 420 |
| cgggaaactg gacggtccgt gacctggcgc agaggatacg gtttccgtct gaccagacga | 480 |
| acggacggtc cgcacgtgcg cagggacaac ggagttcgcc gaacagtacc tggatcttgc | 540 |
| tctccggaga gacccgtcga ggaagagaaa tcctaggatt tgtcttgaaa tcagtaggcc | 600 |
| acctaagacg cctctaaacg agagaggtga agattagaga gagaaaacta tgttactgtc | 660 |
| tactcctagg ggaaaaggta aataacagaa gataatttga ttattgattc gattgttggt | 720 |
| tcttcaatcg gtcgtacccc tcaaatatat aaggggggtc tagatccatt ccaaaacgtt | 780 |
| ctccaacagc tcccacggga ttaaagggct aaacacacga ggagatagaa attttaaccg | 840 |
| cttgatttga tctattcgtg gaccgtctgc acctatgggc ggaccatcca cgggccggac | 900 |
| catttagccg tgctcagtgt cacaaatgga gctcaacaca tgccctcctg cctttaggag | 960 |

```
aagctgagcg aaccaaaagc actgacacag gccggaaccg actcgaaatg ttcacatcgg   1020
ttctcttaag catctgccac atactagatg acgttaacag aaaatcacgt caacgtctgc   1080
acagtcatgg ctcgcccgag gtctccccag gatggcctcg cgcgagcgtg actgtgtctc   1140
ccgtccgagg gtggcctcaa gcgacaaaca tagaaccatg atgtactata gatctatatc   1200
tatgtttaca gtacatcaac agattatgaa gtctatttca ggttgaatga ggtttatcct   1260
cggacgagtg atatttgtcg tttcatattt atgttttata taaattttta ctctcgacac   1320
aatgcattgt cacataccga ttcaaattca aatatatgtg cgattctgtg ctcatattgt   1380
gcgattctgc gctcatatgg cacctatgtt tatgacagtg aaactcacaa tgtttattct   1440
attgacattc attttcatgc aaattacata acgtatgcta gaaccaaatg caaattactg   1500
ctaataaaca tcctgcgtaa gcgcaatggc gcaccattta ccaatagctg taacggtgca   1560
agtacgtaat agttggagcg ttatgtttct ctcctctctt cccaccgtac aggatcatat   1620
atatacacat gcctctagaa cggcttcaat atatagttcc accacattac ttccatatat   1680
ttcccttgga ttggatcgtc ggcgccaaaa cgaataataa tccggca              1727
```

```
<210> SEQ ID NO 32
<211> LENGTH: 21
<212> TYPE: DNA
<213> ORGANISM: Zea mays

<400> SEQUENCE: 32
cccttggatt ggattggatc g                                             21

<210> SEQ ID NO 33
<211> LENGTH: 20
<212> TYPE: DNA
<213> ORGANISM: Zea mays

<400> SEQUENCE: 33
accaccggtt tcctgctgtc                                               20

<210> SEQ ID NO 34
<211> LENGTH: 21
<212> TYPE: DNA
<213> ORGANISM: Zea mays

<400> SEQUENCE: 34
tcttcacgag ggaagctgtc t                                             21

<210> SEQ ID NO 35
<211> LENGTH: 20
<212> TYPE: DNA
<213> ORGANISM: Zea mays

<400> SEQUENCE: 35
gcactgcacc caccgctctt                                               20

<210> SEQ ID NO 36
<211> LENGTH: 22
<212> TYPE: DNA
<213> ORGANISM: Zea mays

<400> SEQUENCE: 36
gtaatacgac tcactatagg gc                                            22

<210> SEQ ID NO 37
```

-continued

```
<211> LENGTH: 27
<212> TYPE: DNA
<213> ORGANISM: Zea mays

<400> SEQUENCE: 37
cttgacgcag tagcagagaa tcccgtc                                        27

<210> SEQ ID NO 38
<211> LENGTH: 26
<212> TYPE: DNA
<213> ORGANISM: Zea mays

<400> SEQUENCE: 38
cagtagtccg accgcacgca cagrtg                                         26

<210> SEQ ID NO 39
<211> LENGTH: 19
<212> TYPE: DNA
<213> ORGANISM: Zea mays

<400> SEQUENCE: 39
actatagggc acgcgtggt                                                 19

<210> SEQ ID NO 40
<211> LENGTH: 30
<212> TYPE: DNA
<213> ORGANISM: Zea mays

<400> SEQUENCE: 40
cagacagctt ccctcgtgaa gctcccattg                                     30

<210> SEQ ID NO 41
<211> LENGTH: 28
<212> TYPE: DNA
<213> ORGANISM: Zea mays

<400> SEQUENCE: 41
tctgygtcag gcagtckcgt gcctcaac                                       28

<210> SEQ ID NO 42
<211> LENGTH: 21
<212> TYPE: DNA
<213> ORGANISM: Zea mays

<400> SEQUENCE: 42
gtcattacca ccacagactt c                                              21

<210> SEQ ID NO 43
<211> LENGTH: 20
<212> TYPE: DNA
<213> ORGANISM: Zea mays

<400> SEQUENCE: 43
actcatgagg tagtgacatt                                                20

<210> SEQ ID NO 44
<211> LENGTH: 20
<212> TYPE: DNA
<213> ORGANISM: Zea mays

<400> SEQUENCE: 44
catttagcag gtcactgtac                                                20
```

```
<210> SEQ ID NO 45
<211> LENGTH: 1594
<212> TYPE: DNA
<213> ORGANISM: Zea mays

<400> SEQUENCE: 45
gttattggtt attgatctac tggtcatgta ctcatgtcat ttagatgtaa ggtcagattt      60
gttcatttgt acgtattatt taggtgccgt gaatgtgaag cgaatgtctc tgtatgcgtg     120
tgagttgggt gccgtagttc tgatgagcgc atgtggatat atactatgta tatatgacac     180
gacacaaaac ttcagtacag cgatggattg tatttatacc ggtttggaat cagaatgcag     240
catcctgttt ttttttggat tgattgatcc tgcatgcatg gccgtgtgtt gggggaatct     300
gagcgtcaat cactgtgatg agtatcagtg gtggtgcttt ctgtgaaggc acggacggtc     360
cgcaacggga aactggacgg tccgtgacct ggcgcagagg atacggtttc cgtctgacca     420
gacgaacgga cggtccgcac gtgcgcaggg acaacggagt tcgccgaaca gtacctggat     480
cttgctctcc ggagagaccc gtcgaggaag agaaatccta ggatttgtct tgaaatcagt     540
aggccaccta agacgcctct aaacgagaga ggtgaagatt agagagagaa aactatgtta     600
ctgtctactc ctaggggaaa aggtaaataa cagaagataa tttgattatt gattcgattg     660
ttggttcttc aatcggtcgt accoctcaaa tatataaggg gggtctagat ccattccaaa     720
acgttctcca acagctccca cgggattaaa gggctaaaca cacgaggaga tagaaatttt     780
aaccgcttga tttgatctat tcgtggaccg tctgcaccta tgggcggacc atccacgggc     840
cggaccattt agccgtgctc agtgtcacaa atggagctca acacatgccc tcctgccttt     900
aggagaagct gagcgaacca aaagcactga cacaggccgg aaccgactcg aaatgttcac     960
atcggttctc ttaagcatct gccacatact agatgacgtt aacagaaaat cacgtcaacg    1020
tctgcacagt catggctcgc ccgaggtctc cccaggatgg cctcgcgcga gcgtgactgt    1080
gtctcccgtc cgagggtggc ctcaagcgac aaacatagaa ccatgatgta ctatagatct    1140
atatctatgt ttacagtaca tcaacagatt atgaagtcta tttcaggttg aatgaggttt    1200
atcctcggac gagtgatatt tgtcgtttca tatttatgtt ttatataaat ttttactctc    1260
gacacaatgc attgtcacat accgattcaa attcaaatat atgtgcgatt ctgtgctcat    1320
attgtgcgat tctgcgctca tatggcacct atgtttatga cagtgaaact cacaatgttt    1380
attctattga cattcatttt catgcaaatt acataacgta tgctagaacc aaatgcaaat    1440
tactgctaat aaacatcctg cgtaagcgca atggcgcacc atttaccaat agctgtaacg    1500
gtgcaagtac gtaatagttg gagcgttatg tttctctcct ctcttcccac cgtacaggat    1560
catatatata cacatgcctc tagaacggct tcaa                                1594
```

EMBRYO SAC-SPECIFIC GENES

The present invention relates to isolated nucleotide sequences useful for the production of plants with a modified embryo and/or endosperm development, to vectors containing the nucleotide sequences, to proteins encoded by the nucleotide sequences, to methods for obtaining the nucleotide sequences, to methods for isolating embryo sac-specific genes or proteins from a plant and to methods for producing agronomically interesting plants exhibiting female sterility or allowing apomictic propagation.

Diploid sporophytic and haploid gametophytic generations alternate in the life cycle of higher and lower plant species. In contrast to lower plant species such as mosses or green algae in which the haploid gametophyte is the dominant generation, the gametophyte in higher plant species is dramatically reduced (Reiser and Fischer, 1993; Drews et al., 1998). Both male (pollen) and female (embryo sac) gametophytes have developed from spores, the haploid products of meiosis from spores (micro- and megaspores). In angiosperms, male gametophytes (pollen) are simple two to three-celled organisms consisting of one vegetative and one or two sperm cells, which are species-specific (Bedinger, 1992; McCormick, 1993). Three of the four megaspores in most angiosperms degenerate and the surviving one forms the female gametophyte after three mitotic divisions (Reiser and Fischer, 1993; Russel, 1993). The predominant female gametophyte, the Polygonium type, which occurs in about 70% of the angiosperm species (Webb and Gunning, 1990; Reiser and Fischer, 1993), is deeply embedded in sporophytic tissue and consists of only seven cells: the egg cell, two synergids, a central cell and three antipodals. In maize and several other species, the antipodal cells continue to proliferate until a group of about 20 to 40 cells is formed (Kiesselbach, 1949).

The main function of the gametophytes is to supply the gametes: male and female gametes fuse during fertilisation, combine their different genomes, and thus form a new sporohytic generation. Thus, sexual reproduction in angiosperms is initiated when pollen grains start to germinate on the female flower organ, the stigma (Cheung, 1996). The female gametophyte might then function in (i) directing the pollen tube to the ovule (Hülskamp et al., 1995; Ray et al., 1997), (ii) directing one sperm cell to the egg cell and the other to the central cell (Russel, 1992), (iii) generating a barrier to polyspermy (Faure et al., 1994; Kranz et al., 1995), (iv) preventing autonomous embryo (parthenogenesis) and endosperm development-(Grossniklaus et al., 1998; Luo et al., 1999; Ohad et al., 1999) and finally (v) accumulating stores of maternal mRNAS to facilitate the rapid initiation of embryo and endosperm development after fertilisation (Dresselhaus et al., 1999b).

Morphological and structural studies of female gametophyte development as well as fertilisation and early embryo/endosperm development have been employed with many plant species (e.g. with maize: Kiesselbach, 1949; Diboll 1968; Huang and Sheridan, 1994 and Arabidopsis: Webb and Gunning, 1990, 1991; Muriga et al., 1993). In contrast, "The identities and specific functions of the haploid-expressed genes required by the female gametophyte are almost completely unknown" (Drews et al., 1998). This reflects the technical difficulty of identifying mutants and of gaining access to certain developmental stages for molecular analyses.

Many mutants have been described that affect female gametophyte development and function, especially in maize and Arabidopsis, suggesting that a large number of loci is essential for embryo sac development (Vollbrecht and Hake, 1995; Drews et al. 1998; Grossniklaus and Schneitz, 1998). A few maternal genes functioning in the embryo sac as repressors of autonomous embryo (pathenogenesis) and/or endosperm development have been recently cloned in Arabidopsis. Mea/fis1 (medea/fertilisation independent seed 1) is a gametophyte maternal effect gene probably involved in regulating cell proliferation in endosperm and partially in the embryo as well (Grossniklaus et al., 1998; Luo et al., 1999). Fis2 shows a similar phenotype and encodes a putative zinc-finger transcription factor (Luo et al., 1999): Autonomous endosperm development was observed in the fie (fertilisation independent endosperm/fis3 mutant. Mea/fis1 and fie/fis3 display homology to polycomb proteins (Grossniklaus et al. 1998; Ohad et al., 1999), proteins which are involved in long-term repression of homeotic genes in Drosophila and mammalian embryo development (Pirrotta, 1998).

At a low frequency, auxin (2,4 D) treated sexual eggs from maize can be triggered to initiate embryo development (Kranz et al., 1995), and some egg cells initiate parthenogenetic development spontaneously. In wheat, lines have been described producing up to 90% parthenogenetic haploids (Matzk et al., 1995). The molecular mechanisms underlying these processes are completely unknown. One protein α-tubulin) was identified whose expression is associated with the initiation of parthenogenesis in wheat (Matzk et al., 1997). De novo transcription from the zygotic genome occurs relatively soon after fertilisation in maize (Sauter et al., 1998; Dresselhaus et al., 1999a), indicating that the store of maternal mRNA and the maternal control of embryo development is not as relevant as it is in animal species, for example *Drosophila, Xenopus* or Zebrafish (Orr-Weaver 1994; Newport and Kirschner 1982; Zamir et al. 1997).

An important biological process linked to flower and seed development is apomixis (asexual reproduction through seeds: Koltunow et al., 1995; Vielle-Calzada et al., 1996). Due to the enormous economical potential of apomixis once controllable in sexual crops, its application was named after the 'Green Revolution' as the 'Asexual Revolution' (Vielle-Calzada et al., 1996). Up to now all approaches to isolate the 'apomixis genes' from apomictic species failed. Genes involved in autonomous endosperm development once inactivated were recently isolated from Arabidopsis (see Ohad et al., 1999; Luo et al., 1999). Autonomous embryo development (via parthenogenesis), a further component of apomixis will be necessary to engineer the apomixis trait in sexual crops. E.g. in wheat, lines have been described producing up to 90% parthenogenetic haploids (Matzk et al., 1995). Almost no molecular data concerning parthenogenesis is available for higher plants: one protein (α-tubulin) was identified from the above described wheat lines whose expression is associated with the initiation of parthenogenesis (Matzk et al., 1997). Nevertheless, such a 'house keeping gene' will not be a valuable tool for genetic engineering of the induction of parthenogenesis. Regulatory genes are needed.

Thus, from an agronomical point of view it is highly desirable to provide plants, in particular agronomically important plants, which allow improved hybrid breeding, apomictic propagation and/or plants having seedless fruits, as well as providing female sterile plants.

Thus, it is considered particularly important to develop and provide means and methods that allow the production of plants exhibiting a modified embryo and endosperm development, in particular plants exhibiting a modified female gametophyte development. Such plants may prove particularly useful in commercial breeding programmes.

The technical problem underlying the present invention is to provide nucleotide sequences and proteins for use in cloning and expressing genes involved in embryo and endosperm development, in particular for use in monocotyledonous plants which allow for the production of plants with a modified embryo and endosperm development, in particular which allow the production of female sterile plants or plants capable of apomictic propagation.

DETAILED DESCRIPTION OF THE INVENTION

The present invention solves the technical problem underlying the present invention by providing isolated and purified nucleotide sequences for use in cloning or expressing an embryo sac-specific nucleotide sequence selected from the group consisting of a) the nucleotide sequence defined in any one of SEQ ID No. 1 to 8 and SEQ ID No. 13 to 31, a part or a complementary strand thereof, b) a nucleotide sequence which hybridises to the nucleotide sequence defined in a), a part or a complementary strand thereof, c) a nucleotide sequence which is degenerated as a result of the genetic code to the nucleotide sequence defined in a), b), a part or a complementary strand thereof and d) alleles, functional equivalents or derivatives of the nucleotide sequence defined in a), b), c), a part or a complementary strand thereof.

The nucleotide sequences set out in SEQ ID No. 1 to 8 and 13 to 31 represent nucleotide sequences which are essential for embryo and endosperm development, and which are active in the mature embryo sac of plants, such as maize. Thus, the present invention is inter alia based upon the finding, isolation and characterisation of genes, in the following also termed ZmES (Zea mays embryo sac) genes, which are specifically expressed in the cells of female gametophytes of a higher plant species, in particular in the ovary or mature egg apparatus, e.g. egg cell, central cell and synergides. Expression of the genes of the present invention in cells outside the female gametophyte was not detected. Furthermore, the ZmES genes of the present invention are expressed in a temporarily specific manner, in particular their expression is switched off after fertilisation and expression cannot he detected in the 2-cell or subsequent embryo stages.

The nucleotide sequence as set out in SEQ ID No. 1 to 8 and 13 to 31 represent nucleotide sequences, in particular DNA sequences for use in cloning or expressing an embryo sac-specific nucleotide sequence which is essential for embryogenesis and endosperm development and is active in the embryo sac. Thus, these nucleotide sequences play a particularly important role in embryogenesis and gametophyte development. Accordingly, the nucleotide sequences of the present invention are useful for cloning, in particular isolating, embryo sac-specific nucleotide sequences, in particular regulatory elements, gene transcripts, coding sequences and/or full length genes in plants, in particular in monocotyledonous plants. Thus, the present invention provides a means for the isolation of embryo sac-specific coding sequences and/or transcription regulatory elements as well as gene transcripts that direct or contribute to embryo sac-specific preferred gene expression in plants, in particular in monocotyledonous plants, such as maize.

The nucleotide sequences of the present invention are both regulatory and protein coding nucleotide sequences.

The present invention thus relates to nucleotide sequences which are regulatory sequences, in particular transcription regulatory elements capable of directing embryo sac-specific expression of a nucleotide sequence of interest, the regulatory sequence being selected from the group consisting of a) the nucleotide sequence defined in any one of SEQ ID No. 13 to 31, a part or a complementary strand thereof, b) the nucleotide sequence which hybridise to the nucleotide sequence defined in a), a part or a complementary strand thereof and c) the alleles, functional equivalents or derivatives of the nucleotide sequence defined in a) or b), a part or a complementary strand thereof.

The regulatory sequences, in particular transcription regulatory sequences, are 5' or 3' regulatory sequences for instance promoters, transcribed, but untranslated regions (UTR) enhancers, or 3' transcription termination signals and may prove particularly useful in directing embryo sac-specific expression of genes, in particular protein coding sequences, of interest in plants including the protein coding sequences of the present invention. They are in particular useful for directing embryo sac-specific transcription of heterologous structural and/or regulatory genes in plants, for instance DNA sequences encoding proteins modulating, inducing, repressing or suppressing embryogenesis and/or endosperm development, e.g. Mea/Fis1, Fis2, Fie/Fis3, PICKLE, LEC1 or BBM1 (Grossniklaus et al., 1998; Luo et al., 1999; Chad et al., 1999; Ogas et al., 1999; Lotan et al., 1998; Boutilier et al., unpublished).

Thus, the present invention provides regulatory elements such as promoters, enhancers, UTRs and 3' transcription termination signals providing for embryo sac-specific expression of a gene of interest including the ZmES coding sequences of the present invention. Further, regulatory elements of this specificity may be obtained by using the nucleotide sequences of the present invention to isolate in a genomic DNA library hybridising sequences encompassing further regulatory elements.

In a particularly preferred embodiment of the present invention the above defined promoter of the present invention is expressed in a spatially and temporally specific manner, preferably in the embryo sac. Accordingly, the proteins encoded by a gene of interest cloned downstream from the promoter may be accumulated in embryo sacs or fruits. In a further particularly preferred embodiment, the present invention relates to a DNA construct with a promoter, enhancer, UTR and/or a 3' regulatory element of the present invention operably linked to a coding sequence for a toxic protein such as Diphteria toxin A, Exotoxin A, Barnase or RNase T1 (Day et al., 1995; Koning et al., 1992; Mariani et al., 1990) specifically inhibiting the formation of embryo sac tissue. The genes of interest or coding sequences of interest and/or transcribed but untranslated regions (UTR) of interest may be cloned in sense or antisense orientation to the regulatory sequences of the present invention.

The transcription regulatory elements of the present invention exhibiting the above identified embryo sac-specificity, that is for instance embryo sac-specific promoters of the present invention, may be combined to nucleotide sequences encoding proteins capable of inducing or repressing embryogenesis and/or endosperm development. Inducing embryogenesis and/or endosperm development may prove particularly useful for the production of plants, for example hybrid plants capable of apomictic propagation, that is propagation without fertilisation. The production of plants exhibiting a repressed and/or abortive embryo and/or endosperm development allows the production of for instance female sterile plants. Such plants may form sterile seed or seedless fruit. Thus, the present invention may prove useful for all economically important plants which up until now have not been capable of apomixis and/or plants which do not provide naturally occurring female sterility. The nucleotide sequences of the present invention are useful for expressing or suppressing an embryo sac-specific protein and/or its coding sequence of plants such as monocotyledonous, such as maize or dicotyledonous plants such as sugar beet, including but not limited to the proteins or coding sequences of the present invention. The nucleotide sequences of the present invention are accordingly in a particularly preferred embodiment useful for expressing or suppressing an embryo sac-specific protein, namely the ZmES protein or mutant variants thereof and its target genes in plants, in particular in the embryo sac of plants. Thus, the present invention also provides a means to allow the expression or suppression of a particular embryo sac-specific or embryo sac-abundant gene in the embryo sac, thereby enabling the modification of the embryo sac and endosperm development, function and/or structure. As explained above, the present invention thereby allows the production of plants, the embryos of which develop into plants without fertilisation and allow apomixis, that is the asexual production of seeds.

The present invention also relates to isolated and purified nucleotide sequences which encode a protein capable of modulating embryogenesis and endosperm development, function and/or structure in plants selected from the group consisting of a) the nucleotide sequence of any one of SEQ ID No. 5 to 8 and SEQ ID No. 13 and 14, a part or a complementary strand thereof, b) the nucleotide sequence encoding the amino acid sequence of any one of SEQ ID No. 9 to 12, a part or a complementary strand thereof, c) the nucleotide sequence which hybridise to the nucleotide sequence defined in a), b), a part or a complementary strand thereof, d) the nucleotide sequence which is degenerated as a result of the genetic code to the nucleotide sequence defined a), b), c), a part or a complementary strand thereof, and e) the alleles, functional equivalents or derivatives of the nucleotide sequence defined in a), b), c), d), a part or a complementary strand thereof.

The nucleotide sequences specifically set out in SEQ ID No. 5 to 8 and SEQ ID No. 13 and 14 represent nucleotide sequences encoding a protein, in the following termed the ZmES protein, which is essential for embryo and endosperm formation. ZmES proteins are small, cysteine-rich proteins with an N-terminal signal peptide, most likely for translocation outside the cell. The ZmES proteins of the present invention, namely ZmES1, 2, 3 and 4 are highly homologous to each other.

The protein coding nucleotide sequences of the present invention may be useful in engineering genetically manipulated plants exhibiting a modified embryogenesis and/or endosperm development, function and/or structure. In particular the proteins encoded by the present nucleotide sequences may be considered to be defensins. Defensins appear to be involved in resistance systems against bacterial and fungal pathogens. Thus, the present invention may allow the specific modification of plants, the embryos of which exhibit a modified resistance, in particular improved resistance, against pathogens, for instance microbial pathogens. Of course, the present invention also relates to plants and methods for their production which exhibit a modified resistance, in particular improved resistance against pathogens compared to a non-modified and non-transformed plant.

Plant defensins contain an N-terminal signal peptide and the mature peptides form four disulfide bridges. This protein family includes γ-thionins, proteinase inhibitors 11 and P322 and other (for review see Broekaert et al., 1995). The present invention provides a novel class of putative plant defensins, which is specifically expressed in the female gametophyte of maize. ZmES1–4 contains all structural components which classify them as plant defensins: they are small proteins, contain N-terminal signal peptides and eight Cys which probably form four intramolecular disulfide bridges, the fourth one linking the N- and C-terminal regions of the mature proteins. The predicted secondary structure displays and α-helix and two β-stands at the same position as in the antifungal protein RsAFP1 from radish seeds, whose three-dimensional structure has been determined by NMR spectrometry. The same three-dimensional structure was also determined for charybdotoxin, a neurotoxin from scorpion (Bontems et al., 1992), although this peptide is shorter at the N- and C-terminus and thus forms only three disulfide bonds. Predicted secondary and tertiary structures differ slightly, but the positions of α-helices, β-stands and eight Cys are conserved in all plant defensins. Mature ZmES proteins are longer than most other defensins, but all additional amino acids are located exclusively in coil-regions, neither in α-helix nor β-stands thus allowing the same three-dimensional structure than RsAFP1. Known plant defensins of diverse monocot and dicot species display higher homology among each other than with ZmES proteins.

The protein coding nucleotide sequences or the UTRs of the present invention may be cloned either in sense or antisense orientation to regulatory elements, such as 5' or 3' regulatory nucleotide sequences, including but not limited to the regulatory nucleotide sequences of the present invention. Thus, using for instance antisense or cosuppression technology the nucleotide sequences of the present invention, such as the protein coding sequences, transcribed, but not translated regions (UTRs) or parts thereof, it is possible to generate plants exhibiting a modified, in particular a distorted embryogenesis and/or endosperm development, function or/and structure. Such a distorted embryogenesis and/or endosperm development may cause female infertility or contribute to generating plants capable of apomixis.

Thus, the present invention also allows the modification of structure or expression of the ZmES gene and/or protein which may lead for instance to parthenogenetic embryo development which is an important component of engineering the apomixis trait. For instance, the coding sequence of the present invention may be overexpressed in transformed plants due to expression under control of a strong constitutive tissue or tissue-specific or regulated promoter. It is also possible to modify the coding sequence of the present invention so as to allow the production of a modified embryo sac-specific ZmES protein which in turn modifies in a desired manner embryo sac development and/or function. Most importantly, the present invention provides a means to specifically inhibit the formation of a protein essential for embryo sac and/or endosperm function or development namely the ZmES protein by transforming plants with antisense constructs comprising all or part of the coding sequence or, transcribed but not translated regions of the ZmES gene or a part thereof in antisense orientation under the control of its wild-type or appropriate other regulatory elements so as to effectively bind to wild-type ZmES mRNA and inhibits its translation. Such a construct may lead upon expression to the abolishment or elimination of the wild-type ZmES function thereby producing modified plants.

Of course, such an eliminating effect of natural gene function may also be obtained using cosuppression technology. Accordingly, the nucleotide sequences of the present invention, cloned in sense orientation to at least one regulatory element, such as a promoter into a suitable vector, are transformed into a plant, which in turn may exhibit a suppressed gene function of a wild-type ZmES gene.

The present invention also relates to processes to restore the antisense effect obtained by using the antisense construct mentioned above. To be able to restore the antisense effect, a further DNA construct comprising an ZmES gene derived nucleic acid sequence in sense orientation under control of a switchable or inducible promoter could be used to transform the plant. After switching on the promoter, the antisense effect might be restored. Another method for restoring the above described elimination effect is to utilise a DNA construct, in particular an antisense or co-suppression construct employing an inducible promoter to control the expression of the nucleic acid sequence derived from a ZmES gene, in particular in the antisense or co-suppression construct, via external factors.

In this context, it has to be understood that the antisense constructs of the present invention may not necessarily comprise all or an essential part of the coding sequence of the present invention in antisense orientation to regulatory elements, but in a particularly preferred embodiment it is sufficient to use parts of the coding sequences or of the UTRs which are considerably shorter than the full length coding sequence. The length of such a sequence must be sufficient to allow effective hybridisation to the target mRNA and may be a minimum length of 50 to 100 nucleotides.

The present invention also relates to nucleotide sequences which hybridise, in particular under stringent conditions to the sequences set out in SEQ ID No. 1 to 8 and 13 to 31. In particular, these sequences have on the nucleotide level a degree of identity of >70% to the sequences of SEQ ID No. 1 to 8 and 13 to 31.

In the context of the present invention, nucleotide sequences which hybridise to the specifically disclosed sequences of SEQ ID No. 1 to 8 and 13 to 31 are sequences which have a degree of 60 to 70% sequence identity to the specifically disclosed sequence of the nucleotide level. In an even more preferred embodiment of the present invention, sequences which are encompassed by the present invention are sequences which have a degree to identity of more than 70%, and even more preferred, more than 80%, 90%, 95% and particularly 99% to the specifically disclosed sequences of the present invention on the nucleotide level.

Thus, the present invention relates to nucleotide sequences, in particular DNA sequences which hybridise under the hybridisation condition as described in Sambrook et al., (1989), in particular under the following conditions, to the sequences specifically disclosed:

Hybridisation buffer: 1 M NaCl; 1% SDS; 10% dextran sulphate; 100 µg/ml ssDNA
Hybridisation temperature: 65° C.
First wash: 2×SSC; 0.5% SDS at room temperature
Second wash: 0.2×SSC; 0.5% SDS at 650 C.

More preferably, the hybridisation conditions are chosen as described above, except that a hybridisation temperature and a second wash temperature of 68° C. and, even more preferred, a hybridisation temperature and a second wash temperature of 70° C. is applied.

Thus, the present invention also comprises nucleotide sequences which are functionally equivalent to the sequences of SEQ ID No. 1 to 8 and 13 to 31, i.e. may have a different sequence but have the same or essentially the same function, in particular sequences which are at least homologous to sequences of SEQ ID No. 1 to 8 and 13 to 31. The invention also relates to alleles and derivatives of the sequences mentioned above which are defined as sequences being essentially similar to the above sequences but comprising, for instance, nucleotide exchanges, substitutions— also by unusual nucleotides—rearrangements, mutations, deletions, insertions, additions or nucleotide modifications and are functionally equivalent to the sequences as set out in SEQ ID No. 1 to 8 and 13 to 31.

In the context of the present invention, a number of general terms shall be utilised as follows.

The term "promoter" refers to a sequence of DNA, usually upstream (5') to the coding sequence of a structural gene, which controls the expression of the coding region by providing the recognition for RNA polymerase and/or other factors required for transcription to start at the correct site. Promoter sequences are necessary, but not always sufficient to drive the expression of the gene.

"Nucleotide sequence" refers to a molecule which can be single or double stranded, composed of monomers (nucleotides) containing a sugar, phosphate and either a purine or pyrimidine. The nucleotide sequence may be cDNA, genomic DNA, or RNA, for instance mRNA.

Thus, the term "nucleotide sequence" refers to a natural or synthetic polymer of DNA or RNA which may be single or double stranded, alternatively containing synthetic, non-natural or altered nucleotide bases capable of incorporation into DNA or RNA polymers. In a particularly preferred embodiment, the nucleotide sequence of the present invention is an isolated and purified nucleic acid molecule.

The term "gene" refers to a DNA sequence that codes for a specific protein and regulatory elements controlling the expression of this DNA sequence.

The term "coding sequence" refers to that portion of a gene encoding a protein, polypeptide, or a portion thereof, and excluding the regulatory sequences which drive the initiation or termination of transcription. The coding sequence and/or the regulatory element may be one normally found in the cell, in which case it is termed "autologous", or it may be one not normally found in a cellular location, in which case it is termed "heterologous".

A heterologous gene may also be composed of autologous elements arranged in an order and/or orientation not normally found in the cell into which it is transferred. A heterologous gene may be derived in whole or in part from any source known to the art, including a bacterial or viral genome or episome, eucaryotic nuclear or plasmid DNA, cDNA or chemically synthesised DNA. The structural gene may constitute an uninterrupted coding region or it may include one or more introns bounded by appropriate splice junctions. The structural gene may be a composite of segments derived from different sources, naturally occurring or synthetic.

By "operably linked" it is meant that a gene and a regulatory sequence are connected in sense or antisense expression in such a way as to permit gene expression when the appropriate molecules (e.g. transcriptional activator proteins) are bound to the regulatory sequence.

The term "vector" refers' to a recombinant DNA construct which may be a plasmid, virus, or autonomously replicating sequence, phage or nucleotide sequence, linear or circular, of a single or double stranded DNA or RNA, derived from any source, in which a number of nucleotide sequences have been joined or recombined into a unique construction which is capable of introducing a promoter fragment and DNA sequence for a selected gene product in sense or antisense orientation along with an appropriate 3' untranslated sequence into a cell.

"Plasmids" are genetic elements that are stably inherited without being a part of the chromosome of their host cell. They may be comprised of DNA or RNA and may be linear or circular. Plasmids code for molecules that ensure their replication and stable inheritance during cell replication, and may encode products of considerable medical, agricultural and environmental importance. For example, they code for toxins that greatly increase the virulence of pathogenic bacteria. They can also encode genes that confer resistance to antibiotics. Plasmids are widely used in molecular biology as vectors to clone and express recombinant genes. Starting plasmids disclosed herein are either commercially available, publicly available, or can be constructed from available plasmids by routine application of well-known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

The term "expression" as used herein is intended to describe the transcription and/or coding of the sequence for the gene product. In the expression, a DNA chain coding for the sequence of gene product is first transcribed to a complementary RNA, which is often an mRNA, and then the thus transcribed mRNA is translated into the above mentioned gene product if the gene product is a protein. However, expression also includes the transcription of DNA inserted in antisense orientation to its regulatory elements. Expression, which is constitutive and possibly further enhanced by an externally controlled promoter fragment, thereby producing multiple copies of mRNA and large quantities of the selected gene product, may also include overproduction of a gene product.

The term "suppression" refers to repression, inhibition or reduction of endogenous gene expression.

The term "directing expression" refers to inducing, controlling, regulating, modulating, contributing or enhancing expression of a nucleotide sequence.

In the context of the present invention, the term "protein" refers to any sequence length of amino acid, irrespective of its length. Thus, within the present invention the term "protein" relates to peptides, polypeptides and proteins. The protein of the present invention may be modified by addition of carbohydrates, fats or other proteins or peptides. The proteins of the present invention may also be modified by addition of isotopes, amino-, acyl-, allyl-, or other groups.

The proteins of the invention that do not occur in nature are isolated. The term "isolated" as used herein, in the context of proteins, refers to a polypeptide which is unaccompanied by at least some of the material with which it is associated in its natural state. The isolated protein constitutes at least 0.5%, preferably at least 5%, more preferably at least 25% and still more preferably at least 50% by weight of the total protein in a given sample. Most preferably the "isolated" protein is substantially free of other proteins, lipids, carbohydrates or other materials with which it is naturally associated, and yields a single major band on a non-reducing polyacrylamide gel. Substantially free means that the protein is at least 75%, preferably at least 85%, more preferably at least 95% and most preferably at least 99% free of other proteins, lipids, carbohydrates or other materials with which it is naturally associated.

"Antibody" refers to a polypeptide substantially encoded by an immunoglobulin gene or immunoglobulin genes, or fragments thereof, which specifically bind and recognise an analyte (antigen). The recognised immunoglobulin genes include the kappa, lambda, alpha, gamma, delta, epsilon and mu constant region genes, as well as the myriad immunoglobulin variable region genes. Antibodies exist, e.g. as intact immunoglobulins or as a number of well characterised fragments produced by digestion with various peptidases. The term "antibody", as used herein, also includes antibody fragments either produced by the modification of whole antibodies or those synthesised de novo using recombinant DNA methodologies. The term "antibody" includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule, can be obtained by treating a whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating a whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York (1988)).

The term "host cell" refers to a cell which has been genetically modified by transfer of a chimeric, heterologous or autologous nucleic acid sequence or its descendants still containing this sequence. These cells are also termed "transgenic cells". In the case of an autologous nucleic acid sequence being transferred, the sequence will be present in the host cell in a higher copy number than naturally occurring.

As used herein, "plant" refers to photosynthetic organisms, such as whole plants including algae, mosses, ferns and plant-derived tissues. "Plant derived tissues" refers to differentiated and undifferentiated tissues of a plant, including nodes, male and female flowers, fruits, pollen, pollen tubes, pollen grains, roots, shoots, shoot meristems, coleoptilar nodes, tassels, leaves, cotyledondous leaves, ovules, tubers, seeds, kernels and various forms of cells in culture, such as intact cells, protoplasts, embryos and callus tissue. Plant-derived tissues may be in plants, or in organs, tissue or cell cultures. A "monocotyledonous plant" refers to a plant whose seeds have only one cotyledon, or organ of the embryo that stores and absorbs food. A "dicotyledonous plant" refers to a plant whose seeds have two cotyledons.

"Transformation" and "transferring" refers to methods to transfer DNA into cells including, but not limited to, biolistic approaches such as particle bombardment, microinjection, whisker technology, permeabilising the cell membrane with various physical (e.g., electroporation) or chemical (e.g., polyethylene glycol, PEG) treatments; the fusion of protoplasts or *Agrobacterium tumefaciens* or rhizogenes mediated transformation. There are no specific requirements for the plasmids used for the injection and electroporation of DNA in plant cells. Plasmids such as pUC derivatives can be used. Selectable markers are not necessary. Depending upon the method for the introduction of desired genes into the plant cell, further DNA sequences may be necessary; if, for example, the Ti or Ri plasmid is used for the transformation of the plant cell, at least the right border, often, however, the right and left border of the Ti and Ri plasmid T-DNA must be linked as flanking region to the genes to be introduced.

If Agrobacteria are used for the transformation, the DNA to be introduced must be cloned into specific plasmids, either into an intermediary vector or into a binary vector. The intermediary vectors can be integrated into the Ti or Ri plasmid of the Agrobacteria due to sequences that are homologous to sequences in the T-DNA by homologous recombination. The Ti or Ri plasmid furthermore contains the vir region necessary for the transfer of the T-DNA into the plant cell. Intermediary vectors cannot replicate in Agrobacteria. By means of a helper plasmid, the intermediary vector can be transferred by means of a conjugation to *Agrobacterium tumefaciens*. Binary vectors can replicate both in *E. coli* and in Agrobacteria, and they contain a selection marker gene and a linker or poly-linker framed by the right and left T-DNA border region. They can be transformed directly into the Agrobacteria (Holsters et al., 1978). The *Agrobacterium* serving as a host cell should contain a plasmid carrying a vir region. The *Agrobacterium* transformed is used for the transformation of plant cells. The use of T-DNA for the transformation of plant cells has been extensively examined and described in EP-A 120 516; Hoekema, (1985); An et al., (1985).

For the transfer of the DNA into the plant cell, plant explants can be co-cultivated with *Agrobacterium tumefaciens* or *Agrobacterium rhizogenes*. From the infected plant material (e.g., pieces of leaf, stem segments, roots, but also protoplasts or plant cells cultivated by suspension) whole plants can be regenerated in a suitable medium, which may contain antibiotics or biocides for the selection of transformed cells.

Alternative systems for the transformation of monocotyledonous plants are the transformation by means of electrically or chemically induced introduction of DNA into protoplasts, the electroporation of partially permeabilised cells, the microinjection of DNA into flowers, the microinjection of DNA into micro-spores and pro-embryos, DNA transfer by whisker technology, the introduction of DNA into germinating pollen and the introduction of DNA into embryos by swelling (Potrykus, (1990)).

While the transformation of dicotyledonous plants via Ti plasmid vector systems with the help of *Agrobacterium tumefaciens* is well-established, more recent research work indicates that monocotyledonous plants are also accessible for transformation by means of vectors based on *Agrobacterium* (Chan et al., (1993); Hiei et al., (1994); Bytebier et al., (1987); Raineri et al., (1990), Gould et al., (1991); Mooney et al., (1991); Lit et al., (1992)).

In fact, several of the above-mentioned transformation systems could be established for various cereals: the electroporation of tissues, the transformation of protoplasts and the DNA transfer by particle bombardment in regenerative tissue and cells (Jähne et al., (1995)). The transformation of wheat has been frequently described in the literature (Maheshwari et al., (1995)) and of maize in Brettschneider et al. (1997) and Ishida et al. (1996).

In a further preferred embodiment, the invention relates to nucleotide sequences specifically hybridising to transcripts of the nucleotide sequences of the present invention. These nucleotide sequences are preferably oligonucleotides having a length of at least 10, particularly preferred of at least 15, most preferred of at least 50 nucleotides. The nucleotide sequences and oligonucleotides of the present invention may be used, for instance as primers for a PCR reaction or be used as components of antisense constructs or of DNA molecules encoding suitable ribozymes.

In a preferred embodiment of the present invention, the nucleotide sequence of the present invention is derived from dicotyledonous or monocotyledonous plants.

In a particularly preferred embodiment of the present invention, the nucleotide sequence is derived from maize (*Zea mays*).

In a preferred embodiment of the present invention, the nucleotide sequence of the present invention is a DNA, cDNA or RNA molecule.

The present invention also relates to a vector comprising the nucleotide sequences according to the above, in particular to a bacterial vector, such as a plasmid or a virus.

The present invention thus also relates to vectors comprising the above-identified nucleotide sequences in particular comprising chimeric DNA constructs or non-chimeric DNA constructs such as the wild-type ZmES gene, or derivatives thereof or parts thereof. The term DNA construct refers to a combination of at least one regulatory element and a coding sequence.

Thus, the present invention relates to recombinant nucleic acid molecules useful in the preparation of plant cells and plants as defined above by genetic engineering. In particular, the invention concerns chimeric DNA constructs comprising a coding DNA sequence coding for a wild-type ZmES protein operably linked to a promoter wherein said promoter is different to the promoter linked to said ZmES coding sequence in the wild-type gene i.e. either is a mutated wild-type promoter or a promoter from another gene and/or species. In a further preferred embodiment, the invention concerns chimeric DNA constructs comprising a modified coding DNA sequence coding for a mutated ZmES protein, wherein the DNA-sequence is operably linked to a promoter which may be different from the promoter linked to said ZmES coding sequence in the wild-type gene or the promoter is the wild-type ZmES promoter.

Of course, the present invention also relates to chimeric antisense constructs comprising a DNA sequence encoding, at least partially, the natural, that is wild-type, or modified ZmES protein, or a part thereof, which is linked to a promoter wherein said promoter is different to the promoter linked to said ZmES coding sequences in the wild-type gene or is the wild-type promoter and wherein the orientation of the coding sequence to the promoter is vice versa to the wild-type orientation. In one embodiment of the present invention the DNA sequence of the present invention used specifically to inhibit via antisense constructs the translation of ZmES expression from the wild-type gene is at least partially not derived from the ZmES coding sequence but rather contains sequences from untranslated regions of the ZmES transcribed region. Both the ZmES coding sequence and the untranslated region of the ZmES gene are also termed ZmES derived sequences. Of course the invention also relates to DNA constructs comprising a DNA sequence coding for the non-chimeric wild-type ZmES protein operably linked to the wild-type promoter. These constructs may be used to transform plant cells and plants for which the DNA construct is autologous, i.e. is the source or natural environment for the DNA construct or for which the DNA construct is heterologous, i.e., is from another species. Plant cells and plants obtained by using the above listed DNA constructs may be characterised by ZmES antisense expression, multiple copies of the above DNA constructs in their genome, that means are characterised by an increased copy number of the ZmES gene in the genome and/or a different location in the genome with respect to the wild-type gene and/or the presence of a foreign gene in their genome.

In the context of the present invention a chimeric DNA construct is thus a DNA sequence composed of different DNA fragments not naturally occurring in this combination. The DNA fragments combined in the chimeric DNA construct may originate from the same species or from different species. For example a DNA fragment coding for an ZmES protein may be operably linked to a DNA fragment representing a promoter from another gene of the same species that provides for an increased expression of the ZmES coding sequence. Preferably however, a DNA fragment coding for an ZmES protein is operably linked to a DNA fragment containing a promoter from another species for instance from another plant species, from a fungus, yeast or from a plant virus or a synthetically produced promoter. A synthetically produced promoter is either a promoter synthesised chemically from nucleotides de novo or a hybrid-promoter spliced together by combining two or more nucleotide sequences from synthetic or natural promoters which are not present in the combined form in any organism. The promoter has to be functional in the plant cell to be transformed with the chimeric DNA construct.

The promoter used in the present invention may be derived from the same or from a different species and may provide for constitutive or regulated expression, in particular positively regulated by internal or external factors. External factors for the regulation of promoters are for example light, heat, chemicals such as inorganic salts, heavy metals or organic compounds such as organic acids, derivatives of these acids, in particular its salts.

Examples of promoters to be used in the context of the present invention are the actin promoter from rice, the cauliflower mosaic virus (CaMV) 19S or 35S promoters, nopaline synthase promoters, pathogenesis-related (PR) protein promoters, the ubiquitin promoter from maize for a constitutive expression, the HMG (High molecular weight glutemin) promoters from wheat, promoters from Zein genes from maize, small subunit of ribulose bisphosphonate carboxylase (ssuRUBISCO) promoters, the 35S transcript promoter from the figworm mosaic virus (FMV 35S), the octopine synthase promoter etc. It is preferred that the particular promoter selected should be capable of causing sufficient expression to result in the production of an effective amount of antisense mRNA or modified or wild-type ZmES protein to produce flower and/or fruit modified plants. Of course for selective expression of the ZmES protein tissue specific promoters may be used. However, in the most preferred embodiment of the present invention, i.e. the ZmES antisense constructs, the promoter may be a constitutive strong promoter, since the embryo sac specificity of the antisense action is confined to the embryo sac due to embryo sac-specific expression of the target, i.e. the wild-type ZmES expression.

The DNA construct of the invention may contain multiple copies of a promoter and/or multiple copies of the DNA coding sequences. In addition the construct may include coding sequences for markers and coding sequences for other peptides such as signal or transit peptides or resistance genes for instance against virus infections or antibiotics.

Useful markers are peptides providing antibiotic or drug resistance for example resistance to phosphinstrycine, hygromycin, kanamycin, G418, gentamycin, lincomycin, methotrexate or glyphosate. These markers can be used to select cells transformed with the chimeric DNA constructs of the invention from untransformed cells. Thus, a useful marker gene is the herbicide resistance gene Pat (phosphinotrycine acetyl transferase). Of course other markers are markers coding peptidic enzymes which can be easily detected by a visible reaction for example a colour reaction for example luciferase, $\beta$-1,3-glucuronidase or $\beta$-galactosidase.

Signal or transit peptides provide the ZmES protein formed on expression of the DNA constructs of the present invention with the ability to be transported to the desired site of action. Examples for transit peptides of the present invention are chloroplast transit peptides or mitochondria transit peptides, especially nuclear recognition/localisation signal peptides and endoplasmatic reticulum signal peptides.

In chimeric DNA constructs containing coding sequences for signal or transit peptides these sequences are usually derived from a plant, for instance from corn, potato, Arabidopsis or tobacco. Preferably, transit peptides and ZmES coding sequences are derived from the same plant, for instance corn. In particular such a chimeric DNA construct comprises a DNA sequence coding for a wild-type ZmES protein and a DNA sequence coding for a transit peptide operably linked to a promoter wherein said promoter is different to the promoter linked to said coding sequences in wild-type gene, but functional in plant cells. In particular, said promoter provides for higher transcription efficiency than the wild-type promoter.

The mRNA produced by a DNA construct of the present invention may advantageously also contain a 5' non-translated leader sequence. This sequence may be derived from the promoter selected to express the gene and can be specifically modified so as to increase translation of the mRNA. The 5' non-translated regions can also be obtained from viral RNAs from suitable eucaryotic genes or a synthetic gene sequence.

Preferably, the coding sequence of the present invention is not only operably linked to 5' regulatory elements, such as promoters, but is additionally linked to other regulatory elements such as enhancers and/or 3' regulatory elements. For instance, the vectors of the present invention may contain functional terminator sequences such as the terminator of the octopine synthase gene from *Agrobacterium tumefaciens*. Further 3' non-translated regions to be used in a chimeric construct of the present invention to cause the addition of polyadenylate nucleotides to the 3' end of the transcribed RNA are the polyadenylation signals of the

*Agrobacterium tumefaciens* nopaline synthase gene (NOS) or from plant genes like the soybean storage protein gene and the small subunit of the ribulose-1,5-bisphosphonate carboxylase (ssuRUBISCO) gene. Of course, also the regulating elements of the present invention deriving from the wild-type ZmES gene may be used.

The vectors of the present invention may also possess functional units effecting the stabilisation of the vector in the host organism, such as bacterial replication origins. Furthermore, the chimeric DNA constructs of the present invention may also encompass introns or part of introns inserted within or outside the coding sequence for the ZmES protein.

In a particularly preferred embodiment of the present invention, the nucleotide sequence e.g. the 5' and/or 3' regulatory elements of the present invention contained in the vector, are operably linked to any desired gene or nucleotide sequence also termed a gene of interest, which in this context may also be a coding sequence which may be a heterologous or autologous gene. Such a gene of interest may be a gene, in particular its coding sequence, conferring for instance disease resistance, draught resistance, insecticide resistance, herbicide resistance, immunity and improved intake of nutrients minerals or water from the soil or a modified metabolism in the plant, particularly its embryo sac. In a particularly preferred embodiment, the vector defined above is comprised of further regulatory elements directing or enhancing expression of the gene of interest, such as 5', 3' or 5' and 3' regulatory elements known in the art. Regulatory elements concerned in the present invention also encompass introns or parts of introns inserted in or outside the gene of interest. In a particularly preferred embodiment of the present invention, the regulatory element is a promoter, in particular the cauliflower mosaic virus (CaMV) 35S promoter or a promoter encoded by the nucleotide sequence selected from the group consisting of SEQ ID No. 13 to 31.

Thus, the nucleotide sequences of the present invention are useful since they enable the embryo sac-specific expression of genes of interest of plants, in particular monocotyledonous plants. Accordingly, plants are enabled to product useful products in their embryo or endosperm. The nucleotide sequence of the present invention may also be useful to regulate the expression of genes of interest depending upon the developmental stage of the transferred cell or tissue. Furthermore, the present invention allows the specific modification of the metabolism in embryogenesis and endosperm development.

In a particularly preferred embodiment of the present invention, the vector furthermore contains T-DNA, in particular the left, the right or both T-DNA borders derived from *Agrobacterium tumefaciens*. Of course, a sequence derived from *Agrobacterium rhizogenes* genes may also be used. The use of T-DNA sequences in the vector of the present invention enables the *Agrobacterium* mediated transformation of cells.

In a preferred embodiment of the present invention, the nucleotide sequence of the present invention, optionally operably linked to regulatory elements, is located within the T-DNA or adjacent to it.

The present invention also relates to a host cell transformed with the nucleotide sequence or the vector of the present invention in a particular plant, yeast or bacterial cells, in particular monocotyledonous or dicotyledonous plant cells. The present invention also relates to cell cultures, tissue, calluses, etc. comprising a cell according to the above, for instance a transgenic cell and its descendants harbouring and preferably expressing the nucleotide sequence or vector of the present invention.

Thus, the present invention relates to transgenic plant cells which were transformed with one or several nucleotide sequences of the present invention as well as to transgenic plant cells originating from such cells. Such plant cells can be distinguished from naturally occurring plant cells by the observation that they contain at least one nucleotide sequence according to the present invention which does not naturally occur in these cells, or by the fact that such a sequence is integrated on the genome of the cell at a location where it does not naturally occur, that is in another genomic region or by the observation that the copy number of the nucleotide sequence is different, in particular higher, than the copy number in naturally occurring plants.

Thus, the present invention also relates to transgenic cells, also called host cells, transformed with the nucleotide sequence or vector of the present invention, in particular plant, yeast, or bacterial cells, in particular monocotyledonous or dicotyledonous plant cells. The present invention also relates to cell cultures, tissue, roots, flowers, calluses, propagation and harvest material, pollen seeds, stamen, cobs, nodes, seedlings, somatic and zygotic embryos etc. comprising a cell according to the above, that is a transgenic cell being stably or transiently transformed and being capable of expressing a nucleotide sequence of the present invention, for instance a regulatory element or a nucleotide sequence for encoding a protein modifying the embryogenesis or endosperm development of the transformed plant. The transgenic plants of the present invention can be regenerated to whole plants according to methods known to the person skilled in the art. The regenerated plant may be chimeric with respect to the incorporated foreign DNA. If the cells containing the foreign DNA develop into either micro- or macrospores, the integrated foreign DNA will in one embodiment of the present invention be transmitted to a sexual progeny. If the cells containing the foreign DNA are somatic cells of the plant, non-chimeric transgenic cells are produced by conventional methods of vegetative propagation either in vivo, e.g. from buds or stem cutting or in vitro following established procedures known in the art.

The present invention also relates to a method of genetically modifying a cell by transforming it with a nucleotide sequence of the present invention or vector according to the above whereby the ZmES1, ZmES2, ZmES3 and/or ZmES4 coding sequence or further gene of interest operably linked to at least one regulatory element expressible in the cell, either according to the present invention or as conventionally used. In particular, the cell being transformed by the method of the present invention is a plant, bacterial or yeast cell. In a particularly preferred embodiment of the present invention, the above method further comprises the regeneration of the transformed cell to a differentiated and, in a preferred embodiment, fertile or non-fertile plant.

In a preferred embodiment of the present invention, the method to transform a cell involves direct up-take of the nucleotide sequence, in particular by microinjection of the nucleotide sequence, electroporation, chemical treatment or particle bombardment.

The present invention also relates to a method of production of a protein having the activity of a protein modulating embryogenesis and/or endosperm development, wherein a host cell of the present invention is cultivated under conditions allowing the synthesis of the protein, and wherein the protein is isolated from the cultivated cell and/or the culture medium. Thus, the present invention also relates to a protein being preparable by a host cell of the invention or obtainable by a method for the production of a protein of the invention.

The present invention also relates to a protein capable of modulating embyogenesis and/or endosperm development and being encoded by the nucleotide sequences of the present invention.

The present invention also relates to derivatives of such a protein having essentially the same biological activity. Such modifications may be modifications due to amino acid substitutions, insertions, deletions, inversions, etc. Such modifications may also be constituted by glycosylation or other types of derivatisation.

The present invention also relates to an antibody or a fragment thereof which is reactive with a protein of the invention. These antibodies may be used to screen expression libraries or to identify clones which produce the protein of the present invention. A used herein, the term "relates to an antibody" relates to detection, activation or inhibition of molecular and cellular pathways induced by the protein of the present invention, in particular to modification of the embryogenesis and/or endosperm development. The term "antibody" relates to bivalent or monovalent molecular entities that have the property of interaction with the protein of the invention. As used herein, "antibody" refers to a protein consisting of one or more polypeptides substantially encoded by immunoglobulin genes or fragments of immunoglobulin genes. Light chains are classified as either kappa or lambda. Heavy chains are classified as gamma, mu alpha, delta or epsilon which in turn define the immunoglobulin classes IgG, IgM, IgA, IgD and IgE, respectively (for details see definition of the terms). The phrase "specifically binds to", when referring to an antibody, refers to a binding reaction which is determinative of the presence of the domain and the presence of a heterogeneous population of proteins or other biologics. Thus, under designated immunoassay conditions, the specified antibody binds to a particular domain and does not bind to a significant degree to other proteins represented in the sample. Specific binding to the domain under such conditions may require an antibody that is selected for its specificity for the protein of the invention. A variety of immunoassay format may be used to select antibodies specifically immuno-reactive with the ZmES1, ZmES2, ZmES3 and/or ZmES4 proteins. For example, solid ELISA immuno-assays are routinely used to select monoclonal antibodies specifically immuno-reactive with the domain. The immuno-assays which can be used include, but are not limited to, competitive and non-competitive assay systems using techniques such as Western blot, radioimmuno-assays, immuno-precipitation assays, precipitation reactions, gel diffusion precipitin reactions, immunodiffusion assays, agglutination assays, complement-fixation assays, immunoradiometric-assays, fluorescent-immunoassays and protein A-immunoassays, to name but a few. Antibodies of the invention specifically bind to one or more epitopes on the protein of the invention. Epitope refers to a region of the protein of the invention bound by an antibody, wherein the binding prevents association of a second antibody to the protein.

In an embodiment of the invention, the antibodies are polyclonal antibodies, monoclonal antibodies and fragments thereof. Antibody fragments encompass those fragments which interact with the protein of the invention. Also encompassed are chimeric antibodies typically produced by recombinant methods wherein a foreign sequence comprises part or all of an antibody which interacts with the protein of the invention. Examples of chimeric antibodies include CDR-grafted antibodies. Also included are antibodies composed of an antibody of an animal and a lectin of an animal or plant, in particular a lectin which recognises a modified carbohydrate of the membrane of cells of embryogenesis and/or endosperm development modified plants. Antibodies of the invention may also have a detectable label attached hereto. Such a label may be a fluorescent (e.g. fluorscein isothiocyanate, FITC) enzymatic (e.g. horse radish oxidates) affinity (e.g. biotin) or isotopic label (e.g. $^{125}$I). Also encompassed by the invention are hybridoma, cell lines producing a monoclonal antibody which interact with a protein of the invention. The antibodies of the present invention are useful in the detection of embryogenesis and/or endosperm modified development of plants. Antibodies may be used as a part of a kit to detect the presence of the protein of the invention in a biological sample. Biological samples include tissue, specimens and intact cells or extracts thereof. Such kits employ antibodies having an attached label to allow for detection. The antibodies are useful for identifying non-modified embryogenesis and/or endosperm development of plants.

In an preferred embodiment of the present invention, the antibody or the fragments thereof is modified, in particular used, oxidised and/or oligomerised.

The present invention also relates to a method for isolating embryo sac-specific genes from a plant, whereby a preferably labelled, for instance radioactively or fluorescently labelled, nucleotide sequence of the invention is used to screen gene libraries containing nucleotide sequences derived from a plant, by hybridising the gene library with the labelled sequences of the present invention and detecting the hybridised probes.

The present invention also relates to a method for isolating embryo sac-specific proteins from a plant, whereby an antibody of the invention is used to screen and to isolate embryo sac-specific proteins derived from the plant.

Thus, the present invention also relates to transgenic plants, parts of a plant, plant tissue, reproductive tissue, plant seeds, plant embryos, plant seedlings, plant propagation material plant harvest material, plant leaves and plant pollen, stamen, cobs, nodes, flowers, plant roots containing the above identified plant cells of the present invention. These plants or plant parts are characterised by, as a minimum, the presence of the heterologous transferred DNA construct of the present invention in the genome, or, in cases where the transferred nucleotide sequence is autologous to the transferred host cell, are characterised by additional copies of the nucleotide sequence of the present invention and/or a different location within the genome. Thus, the present invention also relates to plants, plant tissue, plant reproductive or vegetative tissue, plant seeds, plant seedlings, plant embryos, propagation, harvest material, leaves, nodes, cobs, stamen, fruits, flowers, pollen, roots, calluses, tassels, etc. non-biologically transformed which possess, stably or transiently integrated in the genome of the cells, for instance in the cell nucleus, plastides or mitochondria, heterologous and/or autologous nucleotide sequences containing a) a coding sequence of the present invention and/or b) a regulatory element of the present invention recognised by the polymerases of the cells of the said plant. In a preferred embodiment, the coding sequence of the present invention is operably linked in sense or antisense orientation to at least one regulatory element, for instance the regulatory sequence of the present invention. In a further preferred embodiment a regulatory element, in particular the regulatory sequence of the present invention is operably linked to a coding sequence of a gene of interest cloned in sense or antisense orientation to said regulatory sequence. The teaching of the present invention is therefore applicable to any plant, plant genus or plant species wherein the regulatory elements mentioned are recognised by the polymerases of the cell. Thus, the present invention provides plants of many species, genera, families orders and classes, and is able to recognise the regulatory elements of the present invention or derivatives or parts thereof. Any plant is considered, in particular plants of economic interest, for example plants grown for human or animal nutrition, plants grown for the contents of useful secondary metabolites, plants grown for the content of fibres, and trees and plants of ornamental interest. Examples which do not imply any limitation as to the scope of the present invention are corn, wheat, barley, rice, sorghum, sugarcane, sugar beet, soybean, *Brassica*, sunflower, carrot, tobacco, lettuce, cucumber, tomatoes, potato, cotton, *Arabidopsis, Lolium, Festuca, Dactylis* or poplar.

The present invention also relates to a process, in particular a microbiological process and/or technical process, for producing a plant or reproduction material of said plant, including an heterologous or autologous DNA construct of the present invention stably or transiently integrated therein, and capable of being expressed in said plants or reproduction material, which process comprises transforming cells or tissue of said plants with a DNA construct containing a nucleic acid molecule of the present invention, i.e. a regulatory element which is capable of causing the stable integration of the ZmES derived sequences in particular a coding sequence in said cell or tissue and enabling the sense or antisense expression of a ZmES derived sequence, in particular coding sequence or part thereof in said plant cell or tissue, regenerating plants or reproduction material of said plant or both from the plant cell or tissue transformed with said DNA construct and, optionally, biologically replicating said last mentioned plants or reproduction material or both. The present invention also relates to the above process, wherein instead or in addition to the ZmES derived, in particular coding sequence, a regulatory element of the ZmES gene of the present invention is transformed into a plant, preferably operably linked to a coding sequence of interest.

The present invention also relates to a kit comprising the nucleotide sequence of the present invention and/or the protein of the present invention and/or the antibodies of the present invention. The kit of the present invention is useful in detecting genes involved in embryogenesis and/or endosperm development. The present invention also relates to the use of the nucleotide sequence of the present invention and the protein and/or the antibody of the present invention for the production of embryo and endosperm development in modified plants.

Further preferred embodiments of the present invention are mentioned in the subclaims.

The invention may be more fully understood from the following figures and detailed sequence descriptions, which are part of the present teaching. The SEQ ID No. 1 to 45 are incorporated in the present invention. The numbering for each DNA sequence corresponds to the genomic clone of the gene in question.

(a): Egg and nucellus cells hybridized with a ZmES4 antisense probe.
(b): Egg cell hybridized with a ZmES4 sense probe.
(c): Central cell, synergid and nucellus cells hybridized with a ZmES4 antisense probe.
(d): Central cell and nucellus cells hybridized with a ZmES4 sense probe.
(e), (f) and (g): Acridine orange staining to display total RNA distribution within synergid, central cell and nucellus cells, respectively. Bars: 50 μm.

Figure 5:
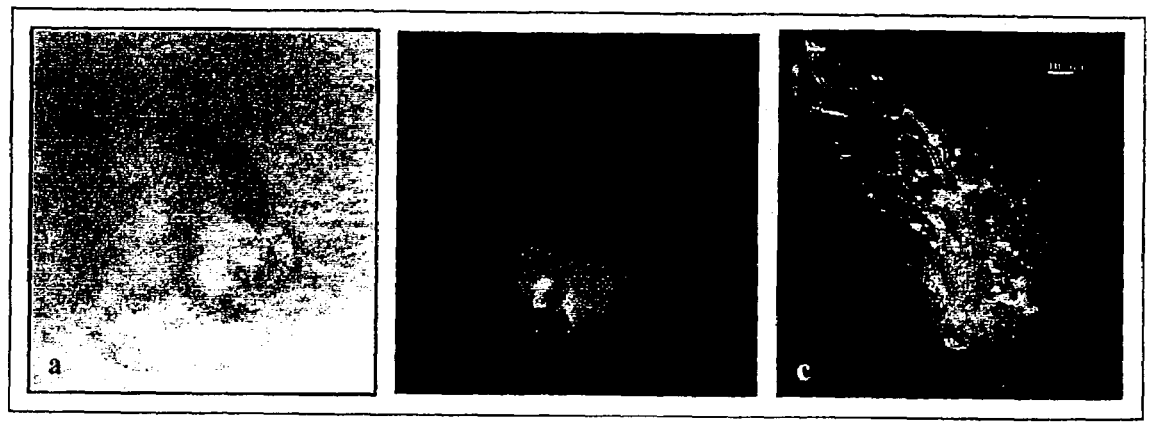

FIG. 5 shows green fluorescence protein (GFP) expression in transgenic maize plants driven by 1594 bp promoter region upstream of the transcription start point of ZmES4.
(a): The expression pattern of ZmES4::GFP fusion protein in the ovary tissue around the embryo sac under light microscopy.
(b): The same preparation as in (a) under UV light microscopy.
(c): The same preparation as in (a) using CLSM.

SEQ ID No. 1 represents the full length cDNA sequence of the ZmES1 (Zea mays embryo sac) gene, from and including position 619 towards the 5' end, up to and including position 1204.

SEQ ID No. 2 represents the full length cDNA sequence of the ZmES2 gene, from and including position 1 towards the 5' end, up to and including position 517.

SEQ ID No. 3 represents the full length cDNA-sequence of the ZmES3 gene, from and including position 1 towards the 5' end, up to and including position 501.

SEQ ID No. 4 represents the full length cDNA sequence of the ZmES4 gene, from and including position 1850 towards the 5' end, up to and including position 2430.

SEQ ID No. 5 represents the protein coding region of ZmES1, from and including position 702 towards the 5' end, up to and including position 977 (excluding the stop-codon).

SEQ ID No. 6 represents the protein coding cDNA region of ZmES2, from and including position 77 towards the 5' end, up to and including position 349 (excluding the stop-codon).

SEQ ID No. 7 represents the protein coding cDNA region of ZmES3, from and including position 78 towards the 5' end, up to and including position 350 (excluding the stop-codon).

SEQ ID No. 8 represents the protein coding region of ZmES4, from and including position 1927 towards the 5' end, up to and including position 2199 (excluding the stop-codon).

SEQ ID No. 9 represents the amino acid sequence of the ZmES1 protein.

SEQ ID No. 10 represents the amino acid sequence of the ZmES2 protein.

SEQ ID No. 11 represents the amino acid sequence of the ZmES3 protein.

SEQ ID No. 12 represents the amino acid sequence of the ZmES4 protein.

SEQ ID No. 13 represents the full length genomic clone of the ZmES1 gene, from and including position 1 towards the 5' end, up to and including position 1204; at the position 587 is a TATA sequence, at the position 702 is a ATG sequence (start codon) at the position 978 is a TAA sequence (stop codon).

SEQ ID No. 14 represents the full length genomic clone of the ZmES4 gene, from and including position 1 towards the 5' end, up to and including position 2430; at the position 1817 is a TATA sequence, at the position 1927 is a ATG sequence (start codon) and at the position 2200 is a TGA sequence (stop codon).

SEQ ID No. 15 represents the full length promoter of the ZmES1 gene, from and including DNA sequence of the position 1 towards the 5' end, up to and including position 701.

SEQ ID No. 16 represents a partial DNA sequence of the promoter of the ZmES1 gene; the sequence spans the region from and including position 501 towards the 5' end, up to and including position 701.

SEQ ID No. 17 represents a partial DNA sequence of the promoter of the ZmES1 gene; the sequence spans the region from and including position 201 towards the 5' end, up to and including position 701.

SEQ ID No. 18 represents the transcribed 5'-untranslated region (UTR) of the ZmES1 gene, from and including position 619 towards the 5' end, up to and including position 701.

SEQ ID No. 19 represents the transcribed 5'-untranslated region of the ZmES2 gene, from and including position 1 towards the 5' end, up to and including position 76.

SEQ ID No. 20 represents the transcribed 5'-untranslated region of the ZmES3 gene, from and including position 1 towards the 5' end, up to and including position 77.

SEQ ID No. 21 represents the transcribed 5'-untranslated region of the ZmES4 gene, from and including position 1850 towards the 5' end, up to and including position 1926.

SEQ ID No. 22 represents the 3'-termination region including the Poly A addition sequence of the ZmES1 gene, from and including position 978 towards the 5' end, up to and including position 1223.

SEQ ID No. 23 represents the 3'-termination region including the Poly A addition sequence of the ZmES2 gene, from and including position 350 towards the 5' end, up to and including position 537.

SEQ ID No. 24 represents the 3'-termination region including the Poly A addition sequence of the ZmES3 gene, from and including position 351 towards the 5' end, up to and including position 519.

SEQ ID No. 25 represents the 3'-termination region including the Poly A addition sequence of the ZmES4 gene, from and including position 2200 towards the 5' end, up to and including position 2449.

SEQ ID No. 26 represents the full length DNA sequence of the promoter of the ZmES4 gene, from and including position 1 towards the 5' end, up to and including position 1926.

SEQ ID No. 27 represents a partial DNA sequence of the promoter of the ZmES4 gene; the sequence spans the region from and including position 1699 toward the 5' end, up to and including position 1926.

SEQ ID No. 28 represents a partial DNA sequence of the ZmES4 gene; the sequence spans the region from and including position 1499 towards the 5' end, up to and including position 1926.

SEQ ID No. 29 represents the partial DNA sequence of the promoter of the ZmES4 gene; the sequence spans the region from and including position 999 towards the 5' end, up to and including position 1926.

SEQ ID No. 30 represents the partial DNA sequence of the promoter of the ZmES4 gene; the sequence spans the region from and including position 499 towards the 5' end, up to and including position 1926.

SEQ ID No. 31 represents the partial DNA sequence of the promoter of the ZmES4 gene; the sequence spans the region from and including position 199 towards the 5' end, up to and including position 1926.

SEQ ID No. 32 to 44 represent primers used in obtaining the ZmES genes.

SEQ ID No. 45 represents a 1594 bp promotor region of ZmES4 that was used for monitoring expression of the promotor of ZmES4 after stable integration into the maize genome.

The following examples are offered to more fully illustrate the invention, but are not construed as limiting the scope thereafter.

EXAMPLES

Materials and Methods Used Throughout the Examples

Plant Material, Isolation of Cells from the Embryo Sac, in vivo and in vitro Fertilisation Maize (*Zea mays*) inbred line A188 (Green and Phillips, 1975) were grown under standard green house conditions.

Cells of the embryo sac were mechanically isolated from digested ovule tissues with glass needles and transferred using a hydraulic microcapillary system according to Kranz et al. (1991). In vitro zygotes were generated after fusing isolated gametes by a short electric pulse and cultivated as described (Kranz and Lörz, 1993). In vivo zygotes were generated as described by Cordts et al. (2001). The cells were collected and fixed on glass slides or stored in 200 nl each at −80° until usage.

Light Microscopy 2 mm thick slices of spikelets were fixed in 4% paraformaldehyde in 0.005 M phosphate buffer, pH 7.2. The slices were washed in 0.1 M phosphate buffer, dehydrated in ethanol series and infiltrated in gradient steps of butyl-methyl methacrylate, followed by UV polymerisation (Wittich and Vreugdenhil, 1998). Sections of 3 µm were made with a Reichert Ultramicrotome, stretched on water, and dried on microscope slides at 60° C. for 1 hour. The resin was removed from the sections by washing the slides in pure acetone for 15 minutes. The slides were then washed in water and sections were stained with toluidine blue (O'Brien et al., 1965).

Differential Plaque- and Reverse Northern Screening

RT-PCR-based cDNA libraries generated from isolated egg cells and in vitro zygotes (Dresselhaus et al., 1994; 1996) were screened by differential plaque screening (Dresselhaus et al., 1996). Double plaque lifts were made from 15 cm plates of the egg cell library at a density of 500 p.f.u. (plaque-forming units). The filters were hybridised either with PCR amplified [$^{32}$P]-cDNA from the egg cell or the zygote cDNA library. cDNA clones from the egg cell library selected by this screening were further analysed by a differential insert screening ("reverse Northern screening"; Dresselhaus et al., 1999 a/b). The cDNA clones were amplified by PCR, separated in agarose gels, blotted and hybridised either with the radiolabelled, PCR amplified cDNA population of the egg cell library or the zygote library. The isolated cDNA clones were further hybridised, with uncloned cDNA populations of egg cells and zygotes as a control. The following gene specific primers were used to specifically amplify the different subgroups of the ZmES gene family: ZmES1 (5'-CCCTTGGATTGGATTGGATCG-3' SEQ ID No. 32 and 5'-ACCACCGGTTTCCTGCTGTC-3' SEQ ID No. 33) and ZmES2/3/4 (5'-TCTTCACGAGG-GAAGCTGTCT-3' SEQ ID No. 34 and 5'-GCACTGCACCCACCGCTCTT-3' SEQ ID No. 35).

RT-PCR

Total RNA from different maize tissues was isolated using TRIZOL® (Gibco-BRL) after the manufacturers recommendations. For quantification, total RNA was separated in a formaldehyd-gel, transferred overnight with 10×SSC to Hybond N$^+$ membranes (Amersham Pharmacia Biotech) and hybridized with a radiolabelled 18S rDNA probe. RNA was quantified using a bioimager system (BAS-1000, Fuji). One µg quantified total RNA of each sample was used for RT-PCR analysis. To avoid amplification from remnant genomic DNA in the sample, total RNA was treated prior RT reaction with DNaseI for 15 min at RT after the manufacturers recommendations (Gibco-BRL). The reaction was stopped by adding EDTA (25 mM) and by incubation for 10 min at 70° C. The PNA was primed with a T$_{14}$-A/G/C-primer (Metabion) and reverse transcribed in 20 µl final volume using 50 U Superscript™ reverse transcriptase (Gibco-BRL) for 60 min. The reaction was stopped by incubating for 10 min at 70° C. Multiplex RT-PCR: 50 µl reactions containing 100 ng of total RNA and the primer pairs for ZmES1 (forward: 5'-CCCTTGGATTGGATTG-GATCG-3' SEQ ID No. 32, reverse: 5'-GTCATTACCAC-CACAGACTTC-3' SEQ ID No. 42) and Zmcdc2 (forward: 5' ACTCATGAGGTAGTGACATT-3' SEQ ID No. 43, reverse: 5'-CATTTAGCAGGTCACTGTAC-3' SEQ ID No. 44; Sauter et al., 1998) were run on a TGradient Cycler (Biometra). 30 cycles, with a first denaturation step at 96° C. for 60 sec, were performed with the following parameters: 96° C. for 30 sec, 58° C. for 30 sec and 72° C. for 60 sec, followed by a final extension at 72° C. for 10 min before soaking at 4° C. Single-cell RT-PCR analysis with one primer pair was carried out as described by Richert et al. (1996) using primers SEQ ID No. 32-35 with a few modifications as described by Cordts et. (2001).

DNA Gel Blot Analyses

Extraction of genomic DNA from 10-day old seedlings was performed according to Dellaporta et al. (1983). 10 µg genomic DNA was digested with the restriction enzymes indicated and resolved on 0.8% agarose gels. DNA was transferred to Hybond N$^+$ membranes (Amersham Pharmacia Biotech) with 0.4 M NaOH. Blots were hybridised with radioactive probes prepared by Prime-It Random Primer Labelling Kit (Stratagene, USA) in CHURCH buffer (7% SDS, 0.5 M NaH$_2$PO$_4$, pH 7.2, 1 mM EDTA) containing 100 µg/ml salmon sperm DNA. Filters were washed with decreasing concentrations of SSC, with a final wash at 65° C. in 0.2×SSC/0.1% SDS. Filters were exposed at −70° C. to Kodak X-Omat AR films using intensifier screens.

In Situ Hybridisation

Ovule pieces containing embryo sacs were fixed in 4% formaldehyde, 0.25% glutaraldehyd and embedded in butyl-methyl-methacrylat (BMM) (Gubler 1989; Baskin et al. 1992). The embedded tissues were sectioned on glass knives with an ultramicrotom at 5 to 7 µm thickness.

A whole mount in situ hybridisation protocol was developed for isolated cells of the embryo sac. Cells were temporarily collected after isolation in 540–650 mosmol kg$^{-1}$ mannitol and then placed in drops of fixation solution (540–650 mosmol kg$^{-1}$ mannitol, 4% formaldehyde, 0.25 glutaraldehyd) on mounted glass coverslides (bindsilane; Wacker-Chemie). The cells were always submerged in liquids. After 30 min incubation, the samples were postfixed for 15 min by adding droplets of PBS-buffer containing 20% acetic acid. The samples were dehydrated by passage through a graded ethanol series (10% to 70%) and stored at 4° C. or directly used for further steps. The solution was gradually substituted with hybridisation solution (10 mM Tris-HCl (pH 7,5), 300 mM NaCl, 50% formamid, 1 mM EDTA, 1× Denharts and 10% dextransulphate) or in Dig-Easy-Hyb (Boehringer Mannheim) containing 250 ng/ml tRNA and 100 µg/ml poly(A) oligonucleotide. The glass cover slides with sticking cells were placed in small (diameter of 35 mm) plastic petri dishes in a volume of 500 µl hybridisation solution. 1 µg/ml labelled probe was added to the hybridisation solution. Washing and detection steps were made by submerging the plastic dishes in larger volumes of the appropriate solutions. Hybridisation, washing steps and detection were performed for sectioned material and whole mount cells in the same manner.

Antisense and sense RNA probes were labelled in vitro from cDNA inserts in pBluescript II SK- with digoxigenin-UTP by T7 or T3 RNA polymerase using a digoxygenin RNA Labelling kit (Boehringer Mannheim). Hybridisation was carried out at 43° C. overnight. Washing steps were performed as follows: 10 min at 43° C., 30 min in 1×SSC/0.01% SDS and once 30 min in 0.5×SSC/0.01% SDS followed by digestion with RNase A (Boehringer, Mannheim). After washing three times in 1% NaCl, detection was made using an anti-digoxigenin antibody conjugated with alkaline phosphatase and NBT/BCIP detection system (Boehringer Mannheim).

DNA and Protein Sequence Analyses

Selected cDNAs were excised from the X ZAP XR vector according to the manufacturer's specifications (Stratagene). All clones were sequenced from both directions using Taq DNA polymerase FS Cycle Sequencing Kit (PE APPLIED BIOSYSTEMS) and the 373A and 377 automated DNA sequences (APPLIED BIOSYSTEMS). DNA and amino acid sequence data were further processed using the PC DNASIS program software package (Hitachi Software Engineering). Sequence data were compiled and compared online with EMBL, GenBank, DDBJ, SwissProt, PIR and PRF databases with FASTA and BLAST algorithms (Pearson, 1990). Protein alignment was performed with the CLUSTAL W program (Thompson et al., 1994). Prediction of protein localization sites was performed online using the PSORT II, and the signal peptide cleavage site was identified after Nielsen et al. (1997). Secondary and tertiary structure prediction was performed and with PDB (Protein Data Bank).

Isolation of Genomic Clones

Genomic DNA was isolated from the maize inbred line A188 according to Dellaporta et al. (1983), partially digested with Sau3A and size fractionated using a saccharose gradient (Sambrook et al., 1989). DNA fragments between 13–23 kb were cloned into the BamHI site of the Lambda Dash II vector (Stratagene) according to the manufacturers specifications. Genomic clones containing ZmES1–4 sequences were identified after using ZmES1–4 cDNA clones as probes.

In order to obtain upstream sequences, the Universal Genome Walker Kit (Clontech) was used. The protocol from the kit was modified as follows: to prepare adaptor ligated DNA, 2.5 µg of λ-DNA was digested in 100 µl reaction volumes with 80 U of different restriction enzymes (Dral, EcoRV, Pvull, Scal and Stul) overnight at 37° C. using buffers recommended by Clontech. The DNA was extracted once with chloroform/isoamyl alcohol (24:1) vol./vol., once with chloroform, and then precipitated by addition of 1/10 (vol/vol) 3 M NaOAc (pH 4.5), 20 µg glycogen and 2 vol. of 95% EtOH. After vortexing, the tubes were immediately centrifuged at 15.000 rpm in a microcentrifuge for 5 min. The pellets were washed with 80% EtOH and immediately centrifuged as above for 5 min, air dried and dissolved in 20 µl of 10 mM Tris-HCl (pH 7.5), 0.1 mM EDTA. From each tube 4 µl of DNA was ligated to an excess of adaptor overnight at 16° C. under the following conditions: 1.9 µl Genome Walker Adaptor (25 µM), 0.5 µl T4 DNA Ligase (1U/µl), 1.6 µl 5×ligation buffer in a total volume of 8 µl. The ligation reaction was terminated by incubation of the tubes at 70° C. for 5 min, then diluted 10-fold by addition of 72 µl of 10 mM Tris-HCl (pH 7.4) and 1 mM EDTA (pH 7.4). The Biometra trioblock was used for all incubation reactions. PCR amplifications were performed using TaqDNA Polymerase (Gibco Life technologies). Primary PCR reactions were conducted in 50 µl volume containing 1 µl of ligated and diluted DNA, 5 µl 10×PCR buffer, 1 µl dNTP (10 mM each), 2.2 µl Mg (OAc)$_2$(25 mM), 1 ml adaptor primer (10 mM) API (5'-GTAATACGACTCACTATAGGGC-3', SEQ ID No. 36) and each 1 µl gene specific primer (10 mM) GSP1 (5'-CTTGACGCAGTAGCAGAGAATCCCGTC-3', SEQ ID No. 37) or GSP2 (5'-CAGTAGTCCGACCG-CACGCACAG(A/g)TG-3', SEQ ID No. 38), and 1.25 U Taq DNA Polymerase. The PCR cycles were conducted as described by the manufacturer. A secondary PCR (nested PCR) reaction was performed with 1 µl of a 100 fold dilution of the primary PCR using adaptor primer AP2 (5'-ACTAT-AGGGCACGCGTGGT-3', SEQ ID No. 39) and nested GSP3 (5'-CAGACAGCTTCCCTCGTGAAGCTC-CCATTG-3', SEQ ID No. 40) and GSP4 (5'-TCTG (c/T) GTCAGGCAGTC(T/g)CGTGCCTCAAC-3', SEQ ID No. 41), respectively. The PCR cycles of the second reaction were conducted as described by the manufacturer. PCR products were cloned using TA cloning vectors (Invitrogen) and sequenced. Upstream sequences of ZmES1 and 4 could thus be cloned. The analysis of the genomic clones and genomic DNA further showed that ZmES1–4 gens contain no introns.

Biolistic Transformation and Analyses of Transgenic Maize Plants 1594 bp promoter region of ZmES4 (SEQ ID No. 45) was used for monitoring expression of the promoter of ZmES4 after stable integration into the maize genome. A construct consisting of SEQ ID No. 45, a part of the cDNA of ZmES4 (bp 2 to bp 351 of SEQ ID No. 4), the coding region of GFP (pMon30049; Monsanto) and the NOS-terminator (McElroy et al., 1995) was generated using the vector Litmus 29 (New England Biolabs). Immature embryos from maize inbred line A188 were isolated 12 days after hand-pollination and co-bombarded with the construct described above and the p35S::pat vector (P. Eckes, Aventis, unpublished) containing phosphinotricin-acetyl-transferase as selection marker. Experimental procedures followed the protocol of Brettschneider et. al. (1997), except that embryos were bombarded with partial vacuum 28 inch Hg and gas pressure 1350 psi. Cultivation, regeneration and selection was carried out as described by Brettschneider et. al. (1997).

GFP Analysis in Transgenic Maize Plants

Immature ears with silks of 15 cm length (counted from bottom part of the ear), were harvested from transgenic plants (lines containing full length integrations of the pZMES::ZMES::GFP::NOS construct as analysed by gel blots; data not shown), kernel were excised and cut in the middle part with razor blades or scalpels. The part of kernels containing the embryo sac was transferred into a 650 mOsm mannitol solution and the nucellar tissue dissected out of the submerged ovary tips. The embryo sac was prepared with fine-tipped glass needles using an inverted microscope. The preparations were analysed by light and UV microscopy, or a Confocal Laser Scanning Microscope (CLSM) for presence of fluorescence in ovary tissues.

Example 1

Isolation of the ZmES Gene Family from Maize Egg Cells

The female gametophyte of maize is deeply embedded in the maternal tissues of the ovule. Gene expression patterns in cDNA libraries of unfertilised egg cells and in vitro zygotes were compared as a starting point for molecular investigations. With the aim of identifying genes completely downregulated after IVF (in vitro fertilisation) and not expressed elsewhere in the plant, 29,000 pfu (plaque forming units) from the egg cell library were analysed. Double plaque lifts were hybridized with the egg cell cDNA population and either with cDNA from in vitro zygotes or cDNA from seedlings. 250 clones were selected and further analysed in reverse Northern blot analysis. 44 different cDNA clones, which were highly represented in the egg cell library and not or weakly in the zygote library, were fully sequenced. Ten cDNAs were highly homologous to each other and were further analysed. These ten cDNAs represent four different genes (ZmES1–4) (see SEQ ID Nos. 1 to 4).

A reverse Northern blot indicates that the whole gene family is completely switched off after IVF and minimal transcript amounts remain detectable 18 h after IVF.

DNA and protein sequence alignments display a high degree of sequence homology among the different ZMES gene family members; even 5' and 3' UTRs (untranslated regions) (SEQ ID No. 18 to 25) are highly conserved. ZmES1 is more distinct from the other ZmES members, both at the DNA and protein level, but all general features, such as transcription start point, two stop codons, putative CPE element and poly(A) signal site at the DNA level, are identical. At the protein level, signal peptide cleavage site and cysteine residues are also identical. The longest cDNA clones of all ZmES members start more or less at the same position with one or two Gs. These Gs are missing in genomic clones of ZmES1 (SEQ ID No. 13) and ZmES4 (SEQ ID No. 14) and most likely result from the $^{7m}G$ cap at the 5' end of all messenger RNAs. This is a strong indication that the isolated cDNAs with SEQ ID No. 1 to 4 are of full length.

Figures 1, 2:
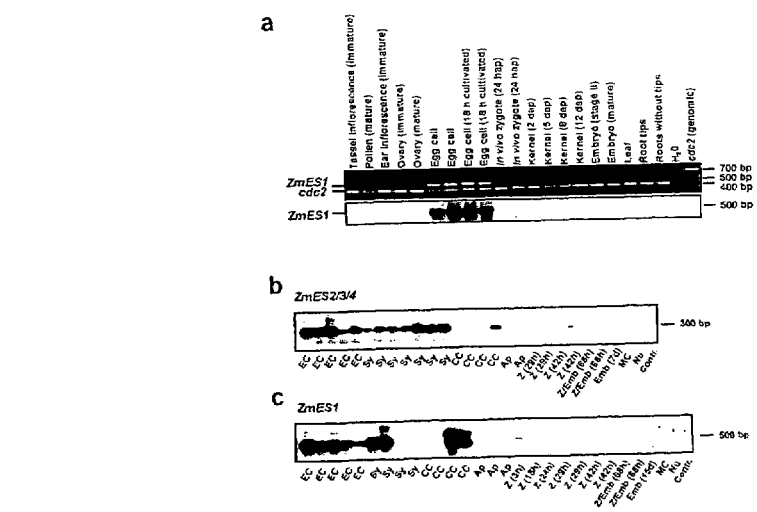
FIG. 1 shows that mature ZmES1–4 peptides display structural homology to defensins.
(a): Homology between mature ZmES1/2 peptides, proteinase inhibitors (PI) and γ-thionins (γThi). N-terminal signal peptides of all proteins show no or few homology among each other and were cleaved of. The consensus sequence of the putative mature peptides is shown below the alignment. Accessions of proteins used to create the alignment are as follows: putative proteinase inhibitors 11 and P322 from *Arabidopsis thaliana, Oryza sativa, Brassica rapa, Solanum tuberosum, Glycine max* (AtPI II: AC005936; OsPI: AAB17095; BrPI II: L31937; StPI P322: P20346; GmPI P322: Q07502), γ-thionins from *Nicotiana tabacum, Picea abies* (NtγThi: P32026; PaγThi: CAA62761) and an α-amylase inhibitor from *Sorghum bicolor* (SbAAI: S13964).
(b): The predicted secondary and tertiary structure of mature ZmES peptides resemble the NMR structure of the plant defensin RsAFP1 from radish and charybdotoxin, a neurotoxin from scorpion. The predicted (pred.) secondary structures are printed in grey (arrows indicate β-strands, cylinder α-helices and lines coil regions). Tertiary structures of mature RsAFP1 seeds (Terras et al., 1995; PDB accession #1AYJ) and charybotoxin (Bontems et al., 1992) have been determined by NMR crystallography (NMR) and are printed in black. The lines below the sequences display the position of four (RsAFP1) or three (charybdotoxin) intramolecular disulfide bridges formed between cysteine residues. The positions of all eight (six in the case of Charybdotoxin) Cys (C) are conserved in peptide sequences shown in (a) and (b) indicating that probably all plant defensins form four intramolecular disulfide bridges and thus probably function as monomers.
FIG. 2 shows the expression of ZmES1–4 in different maize tissues, in embryo sac cells as well as in different stages of in vitro and in in vivo zygotes.
(a): Multiplex RT-PCR analysis using tissues and cells indicated. Gene specific primers were used to amplify cDNA of ZmES1 and Zmcdc2, respectively. Zmcdc2 contains an intron between the primers used. The corresponding genomic DNA was loaded onto the last lane. The ethidiumbromide gel was blotted and hybridized with the full length ZmES1 cDNA (below).
(b) and (c): RT-PCR analysis with cells of the female gametophyte, of the ovule and leaf of maize, which were manually isolated. Different zygote and embryo stages were analysed after IVF. ZmES1 (b) or ZmES2/3/4 (c) transcripts were RT-PCR amplified with gene specific primers in the cells indicated, blotted after gel separation and hybridized with the full length ZmES4 cDNA. AP: antipodals, CC: central cell, EC: egg cell, Emb: embryo (h/d after IVF), MC: leaf mesophyll cell, Nu: nucellus cells, SY: synergid, Z: zygote (h after IVF).

ZmES1–4 encode small proteins of 92 and 91 aa (amino acids), shown in SEQ ID No. 9 to 12, respectively. A putative signal peptide is located at the N-terminus of all proteins. A hydrophobic amino acid cluster at the N-terminus of the precursor protein is framed by two basic and one basic amino acid, respectively. The predicted cleavage site is after position 31 (ZmES1) (SEQ ID No. 9) or 30 (ZmES2/3/4) (SEQ ID Nos. 10–12). It is further predicted that the proteins are translocated outside the cell, including the cell wall. The MW of ZmES1–4 precursor proteins is 9.7 kDa, and the pI varies between 8.1 and 8.5, and is thus slightly basic. The mature proteins are cysteine-rich and extremely conserved, with little variation at the C-terminus and the predicted MW is 6.5 kDa, while the pI is between 7.9 and 8.3. The structural homology to defensins is shown in FIG. 1.

To investigate the size of the ZmES gene family and their presence in other related genomes, genomic Southern blot analysis with two different maize inbred lines and the diploid maize relative *Tripsacum dactyloides* was performed. All enzymes used do not cut within the cDNA, nor within the corresponding genomic sequences. Four bands were detected in A188, the maize line used to generate the cDNA libraries. The same number of bands was detected in another inbred line (B73), while two to three bands were detected in *Tripsacum*. According to the present invention, the whole gene family from the maize inbred line A188 was isolated.

SEQ ID Nos. 1 to 4 illustrate the full length cDNA sequences, SEQ ID Nos. 5 to 8 the protein coding nucleotide sequences and SEQ ID Nos. 9 to 12 the amino acid sequence of ZmES1 to 4.

SEQ ID Nos. 13 and 14 represent the full length nucleotide sequences of the genomic clone of ZmES1 and 4, thus incorporating in 5' to 3' direction the promoter, the transcribed 5' untranslated region (UTR), the protein coding region and the 3' transcription termination region. SEQ ID Nos. 15 to 17 represent the full length promoter and promoters of reduced length of the ZmES1 gene.

SEQ ID Nos. 18 to 21 represent transcribed, but not translated regions of ZmES1 to 4 possibly functioning as expression modulating elements. The UTR nucleotide sequence elements are included in most of the promoter fragments illustrated in SEQ ID Nos. 13 to 31. However, the present invention also encompasses the promoters and fragments thereof indicated in SEQ ID Nos. 13 to 31 wherein the UTRs of SEQ ID Nos. 18 to 21 are missing.

SEQ ID Nos. 22 to 25 represent the 3' transcription termination sequences of ZmES1 to 4 containing possibly important elements for the regulation of transcription.

SEQ ID Nos. 26 to 31 represent full length promoters and promoters of reduced length capable of promoting and/or enhancing transcription with embryo sac-specificity.

Example 2

ZmES1–4 are Specifically Expressed in all Cells of the Embryo Sac and Switched Off After IVF In order to investigate whether ZmES1–4 are exclusively expressed in egg cells, total RNA, poly(A)$^+$ RNA Northern blot and RT-PCR analysis was performed with many different tissues at distinct developmental stages. No signal was obtained in any tissue tested (see FIG. 2 as an example).

Figure 3:
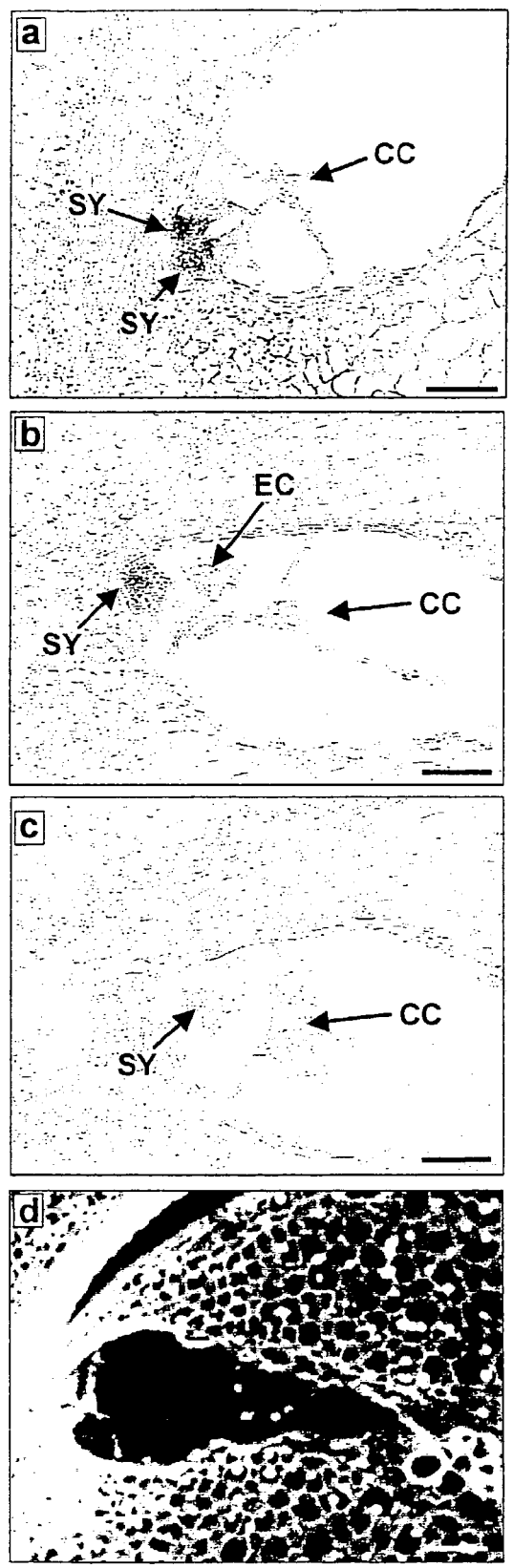
FIG. 3 shows the expression of ZmES in the egg apparatus of maize.
(a) and (b): Median cut sections of ovules containing the embryo sac were hybridized with a ZmES4 antisense probe. A purple signal shows the presence of ZmES4 clearly in the synergids and more faint in the egg and central cell. In nucellus and integuments no signal was detected.
(c): A similar section was hybridized with a ZmES4 sense probe, showing no hybridization signal.
(d): A median cut section of an ovule containing the embryo sac was stained with acridine orange to show nuclei and to monitor RNA content of sections used for in situ hybridization. CC: central cell, EC: egg cell, SY: synergid. Bars: 60 µm.

Tissue in situ hybridisation was performed to investigate the expression of ZmES1–4 in ovules at maturity; strong signals were detected in the cytoplasm of two synergides already after short detection time (see FIG. 3). Signals in nucellus cells, integuments or ovary tissues were never observed. A problem with in situ hybridisation of ovule tissue was that the structure after embedding in paraffin wax and sectioning was not conserved. Tissues had to therefore be embedded in BMM (butyl-methyl-methacrylate), which however only allowed the generation of very thin sections. The structure after BMM embedding is conserved, the sections still contain RNA, but cells contain only few cytoplasm due to the slight thickness of each section, thus making in situ hybridisation less efficient. In addition, all embryo sac cells are very large and highly vacuolated, thus making the detection of transcripts within these cells even more difficult. The embryo sac in its different cell types was therefore dissected and single cell RT-PCR was applied to investigate ZmES1–4 transcript contents.

As shown in FIG. 2 ZmES1–4 transcripts are expressed at comparable levels in all egg cells tested and in most of the synergides and central cells. Some 15 antipodal cells were used under the same RT-PCR conditions for a single reaction, and a much smaller signal was detected, or no signal at all. After IVF, ZmES2/3/4 transcripts were detectable at very low levels in few zygotes up to 42 h after IVF. ZmES1 transcript was detected until 18 h after IVF and 24 h after in vitro pollination in in vivo zygotes. After the first cell division, which generally occurs between 42 and 46 h after IVF, transcripts were no longer detectable. No transcripts could be detected in different embryo stages, in nucellus or leaf mesophyll cells.

Example 3

ZmES1–4 Transcripts are Uniformly Distributed in Cytoplasms of Embryo Sac Cells

Figure 4:
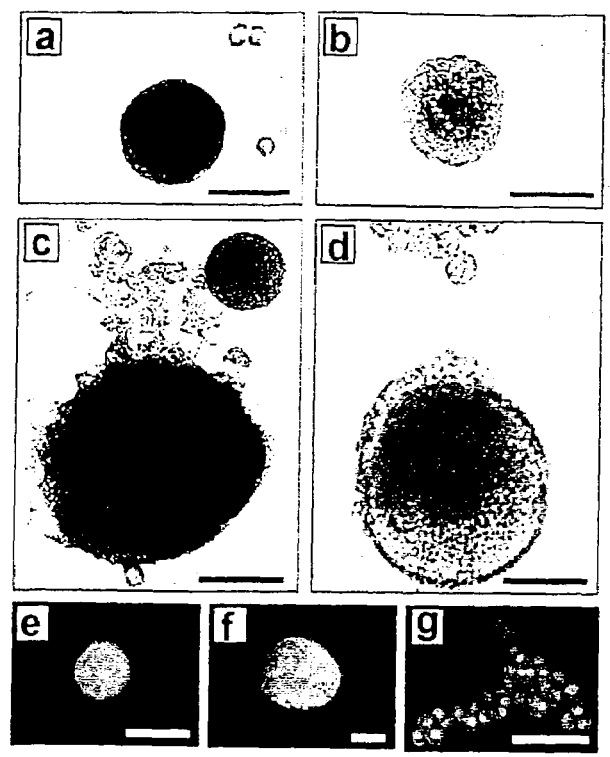
FIG. 4 is a whole mount in situ hybridization showing that ZmES transcripts are uniformly distributed in the cytoplasm of isolated female gametophyte cells.

An in situ hybridisation protocol with isolated embryo sac cells was developed to investigate whether ZmES1–4 transcripts are localized at different poles within the cells of the embryo sac: as shown in FIG. 4 transcripts were detected in egg cells, synergides and central cells. No detection was observed in nucellus cells adjacent to central cells. It seems that ZmES1–4 transcripts are uniformly distributed in these cells, which is best seen in egg cells: in maize egg cells, numerous small vacuoles are located in the periphery of the cells and give no signal. To monitor total RNA distribution, embryo sac and nucellus cells were stained with acridine orange. Total RNA displays a similar pattern than ZmES1–4 transcripts and is uniformly distributed in the cytoplasm of the cells studied.

Example 4

The ZmES4 Promoter is Exclusively Active in Embryo Sac Cells of Transgenic Maize Lines As shown in FIG. 5, some 1.6 kbp upstream of the transcription start point of ZmES4 is sufficient to drive a cell-specific expression of the ZmES4::GFP fusion protein in the cells of the female gametophyte (embryo sac). FIG. 5b shows a signal of the fusion protein in the two synergids and very strong signals around the filiform apparatus. CLSM analysis displays an expression also in the egg and cental cell, but the strongest signals were observed in the region of the egg apparatus. All other cells/tissues of the ovary never showed any fluorescence of the GFP-fusion protein.

REFERENCES

An et al., (1985) EMBO J. 4, 277–287.
Baskin et al., (1992) Planta 187, 405–413.
Bedinger, (1992) Plant Cell 4, 879–887.
Bontems et al., (1992) Biochemistry 31, 7756 ff.
Brettschneider et al., (1997) Theor. Appl. Genet. 94, 737–748.
Broekaert et al., (1995) Plant Physiol. 108, 1353–1358.
Bytebier et al., (1987) Proc. Natl. Acad. Sci. USA 84, 5345–5349.
Chan et al., (1993) Plant Mol. Biol. 22, 491–506.
Cheung, (1996) Trends Plant Sci. 1, 45–51.
Cordts et al., (2001) Plant J. 25, 103–114.
Day et al., (1995) Development 121, 2887–2895.
Dellaporta et al., (1983) Plant Mol. Bio. Rep. 4, 19–21.
Diboll, (1968) Amer. J. Bot. 55, 787–806.
Dresselhaus et al., (1994) Plant J. 5, 605–610.
Dresselhaus et al., (1996) Plant Mol. Biol. 31, 23–34.
Dresselhaus, et el., (1999a) Mol. Gen. Genet. 261, 416–427.
Dresselhaus et al., (1999b) Plant Mol. Biol 39, 1063–1071.
Drews et al., (1998) Plant Cell 10, 5–17.
Faure et al., (1994) Science 263, 1598–1600.
Gould et al., (1991) Plant Physiol. 95, 426–434.
Green and Phillips, (1975) Crop Sci. 15, 417–421.
Grossniklaus and Schneitz, (1998) Semin. Cell. Dev. Biol. 9, 227–238
Grossniklaus et al., (1998) Science 280, 446–450.
Gubler, (1989) Cell Biol. Int. Rep. 13, 137–145.
Hiei et al., (1994) Plant J. 6, 271–282.
Hoekema (1985) The Binary Plant Vector System, Offsetdrukkerij Kanters B. V., Alblasserdam, Chap. V
Holsters et al., (1978) Mol. Gen. Genet. 163, 181–187.
Huang and Sheridan, (1994) Plant Cell 6, 845–861.
Hülskamp et al., (1995) Plant Cell, 7, 57–64.
Ishida et al., (1996) Nature Biotechnology 14, 745–750.
Jähne et al., (1995) Euphytica 85, 35–44.
Kiesselbach, (1949) Cold Spring Harbor, N.Y.: Cold Spring Harbor Laboratory Press.
Koltunow et al., (1995) Plant Physiol. 108, 1345–1352.
Koning et al., (1992) Plant Mol. Biol. 18, 247–258.
Kranz et al., (1991) Sex. Plant Reprod. 4, 12–16.
Kranz and Dresselhaus, (1996) Trends Plant Sci. 1, 82–89.
Kranz and Lörz, (1993) Plant Cell 5, 739–746.
Kranz et al., (1995) Plant J. 8, 9–23.
Lit et al., Plant Mol. Biol. 20 (1992), 1037–1048.
Lotan et al., (1998), Cell 93, 1195–1205.
Luo et al., (1999) Proc. Nat. Acad. Sci. USA 96, 296–301.
Maheshwari et al., (1995) Critical Reviews in Plant Science 14 (2) 149–178.
Mariani et al., (1990) Nature 347, 737–741.
Matzk et al., (1995) Sex. Plant Reprod. 8, 266–272.
Matzk et al., (1997) Hereditas 126, 219–224.
McCormick, (1993) Plant Cell 5, 1265–1275.
McElroy et al., (1995) Molecular Breeding 1, 27–37.
Mooney et al., (1991) Plant Cell Tiss. & Org. Cult. 25, 209–218.
Muriga et al., (1993) Amer. J. Bot. 80, 824–838.
Newport and Kirschner, (1982) Cell 30, 687–696.
Nielsen et al., (1997) Protein Engineering 10, 1–6.
O'Brien et al., (1965) 0. Protoplasma 59, 368–373.
Ogas et al., (1999) Proc. Natl. Acad. Sci. USA 96, 13839–13844.
Ohad et al., (1999) Plant Cell 11, 407–415.
Orr-Weaver, (1994) Trends Genet. 10, 321–327.
Pearson, (1990) San Diego, Calif.: Academic Press Inc., 63–98.
Pirrotta, (1998) Cell 93, 333–336.
Potrykus (1990) Physiol. Plant, 296–273.
Raineri et al., (1990) Bio/Technology 8, 33–38.
Ray et al., (1997) Development, 124, 2489–2498.
Reiser and Fischer, (1993) Plant Cell 5, 1291–1301.
Richert et al., (1996) Plant Sci. 114, 93–99.
Russel, (1993) Plant Cell 5, 1349–1359.
Sambrook et al., (1989) Molecular Cloning: A laboratory manual, Cold Spring Harbor Laboratory Press, New York
Sauter et al., (1998) Sex. Plant Reprod. 11, 41–48.
Thompson et al., (1994) Nucl. Acids Res. 22, 4673–4680.
Vollbrecht and Hake, (1995) Dev. Genetics 16, 44–63.
Vielle-Calzada et al., (1996), Science 274, 1322–1323.
Webb and Gunning, (1990) Sex. Plant Reprod. 3, 244–256.
Webb and Gunning, (1991) Planta 184, 187–195.
Wittich and Vreugdenhil, (1998) J. Exp. Bot. 49, 1163–1171.
Zamir et al., (1997) Mol. Cell. Biol. 17, 529–536.

The invention claimed is:

1. An isolated nucleotide sequence comprising a sequence selected from the group consisting of: SEQ ID NO: 4, 8, or 14.

2. The nucleotide sequence according to claim 1, wherein the nucleotide sequence encodes a regulatory protein having the amino acid sequence of SEQ ID NO: 12.

3. The nucleotide sequence of claim 1 comprising the sequence of SEQ ID NO: 14, or the complementary strand thereof.

4. The nucleotide sequence of claim 1, wherein the sequence is obtained from maize.

5. The nucleotide sequence of claim 1, wherein the sequence is a DNA, cDNA or RNA molecule.

6. A vector comprising the nucleotide sequence of claim 1.

7. The vector of claim 6, which is a bacterial vector or viral vector.

8. The vector of claim 6, wherein the nucleotide sequence of is operably linked to at least one regulatory element in antisense or sense orientation.

9. The vector of claim 6, wherein the regulatory element is a 5' or 3' regulatory element.

10. The vector of claim 9, wherein the 5' regulatory element is a promoter.

11. The vector of claim 9, wherein the 3' regulatory element is a termination and poly-A addition sequence from the NOS gene of *Agrobacterium tumefaciens*.

12. A host cell containing the vector of claim 6.

13. A cell culture comprising the host cell according to claim 12.

14. A method of producing a transgenic plant cell, comprising transforming the plant cell with the nucleotide sequence of claim 1.

15. The method of claim 14, wherein the cell is transformed by direct uptake of at least one nucleotide sequence.

16. A method for the production of a protein for modulating embryogenesis or endosperm development, comprising cultivating the host cell of claim 12 in culture medium under conditions allowing the synthesis of the protein, and isolating the protein.

17. The vector of claim 10, wherein the 5' regulatory element is a CaMV 35S promoter.

18. The vector of claim 10, wherein the 5' regulatory element is a promoter located within the nucleotide sequence of SEQ ID NO: 14.

19. The host cell of claim 12, which is a bacterial cell.

20. The host cell of claim 12, which is a yeast cell.

21. The method of claim 14, wherein the cell is transformed by *Agrobacterium* mediated transformation.

22. The method of claim 14, wherein the cell is transformed by a method selected from the group of methods consisting of microinjection, electroporation, chemical treatment, and particle bombardment.

23. An isolated nucleotide sequence comprising the complementary sequence of SEQ ID NO: 4, 8, or 14.

24. A method of producing transgenic maize cell, comprising transforming the maize cell with a vector comprising the nucleotide sequence of claim 1.

25. A method of producing transgenic maize plant, comprising transforming the plant with a vector comprising the nucleotide sequence of claim 1.

26. The host cell of claim 12, which is an egg cell from maize.

27. A plant comprising the vector of claim 10.

28. Seed comprising the vector of claim 10.

* * * * *